United States Patent [19]

Markaverich et al.

[11] Patent Number: 5,216,024
[45] Date of Patent: Jun. 1, 1993

[54] CELL GROWTH INHIBITORS AND METHODS OF TREATING CANCER AND CELL PROLIFERATIVE DISEASES

[75] Inventors: Barry M. Markaverich, The Woodlands; James H. Clark, Houston; Rebecca Gregory, Houston; Mary Alejandro, Houston; Brian S. Middleditch, Houston; Gregory A. Johnson, Houston; Rajender S. Varma, The Woodlands, all of Tex.

[73] Assignee: Baylor College of Medicine, Houston, Tex.

[21] Appl. No.: 219,680

[22] Filed: Jul. 15, 1988

Related U.S. Application Data

[63] Continuation-in-part of Ser. No. 79,199, Jul. 28, 1987, abandoned.

[51] Int. Cl.$^5$ .......................................... A01N 37/10
[52] U.S. Cl. .................................. 514/543; 514/532; 514/570; 514/678; 514/699; 560/60; 560/55; 560/61; 560/75; 562/465; 562/470; 562/471; 562/478; 568/308; 568/337; 568/442; 568/608; 568/648
[58] Field of Search ............... 514/543, 532, 570, 678, 514/699; 560/60, 55, 61, 75; 562/465, 470, 471, 478; 568/308, 337, 442, 608, 648

[56] References Cited

U.S. PATENT DOCUMENTS

| | | | |
|---|---|---|---|
| 2,451,149 | 10/1948 | Boehm | 514/718 |
| 4,124,724 | 11/1978 | Agoro | 514/570 |
| 4,219,569 | 8/1980 | Glenn | 514/688 |
| 4,248,892 | 2/1981 | Kanamura et al. | 514/570 |
| 4,733,002 | 3/1988 | Yokoyama et al. | 560/55 |

FOREIGN PATENT DOCUMENTS

| | | |
|---|---|---|
| 0082413 | 6/1983 | European Pat. Off. |
| 0270690 | 6/1988 | European Pat. Off. |
| 2336394 | 2/1974 | Fed. Rep. of Germany |
| 2824828 | 2/1979 | Fed. Rep. of Germany |
| 3239156 | 5/1983 | Fed. Rep. of Germany |
| 3415413 | 11/1984 | Fed. Rep. of Germany |
| 2390160 | 5/1978 | France |
| 59-104340 | 6/1984 | Japan |
| 60-222437 | 11/1985 | Japan |
| 60-248645 | 12/1985 | Japan |
| 61-22042 | 1/1986 | Japan |
| 2074575 | 11/1981 | United Kingdom |
| 2191193 | 12/1987 | United Kingdom |

OTHER PUBLICATIONS

J. Biol. Chem. 1988, vol. 263, No. 15, May 25, 1988, pp. 7203–7210 (see abstract).
Edwards, et al., Journal of Medicine Chemistry vol. 33, No. 7 (1990).
Dimmock & Taylor, Journal of Pharmaceutical Sciences, 64: 241 (1975).
Dimmock & Taylor, Journal of Pharmaceutical Sciences, 63: 69 (1974).
Dimmock, et al., Journal of Pharmaceutical Sciencs, 65: 482 (1976).
Smith, et al., Canadian Journal of Chemistry, 51: 1458 (1973).
Smith, et al., Canadian Journal of Chemistry, 50: 871 (1972).
Horakova, et al., Neoplasma, 18: 355–359 (1971).

*Primary Examiner*—Paul J. Killos
*Attorney, Agent, or Firm*—Fulbright & Jaworski

[57] ABSTRACT

The present invention discloses new and useful compounds including methyl p-hydroxyphenyllactate, its analogues, chemical derivatives and chemically related compounds and their use as antitumor agents, as inhibitors of proliferative cell growth and as prophylactic agents to inhibit and prevent cancer and non-malignant cell growth.

78 Claims, 26 Drawing Sheets

P-HYDROXYPHENYLLACTIC ACID (HPLA)

METHYL P-HYDROXYPHENYLLACTIC ACID (MeHPLA)

CELL GROWTH INHIBITORS AND METHODS OF TREATING CANCER AND CELL PROLIFERATIVE DISEASES

The present invention was made utilizing funds of the United States Government. The U.S. Government is therefore granted a royalty-free, nonexclusive, worldwide, paid-up licnese in this invention.

This application is a continuation-in-part of application Ser. No. 07/079199 filed Jul. 28, 1987, now abandoned.

FIELD OF THE INVENTION

This invention relates to the use of new and useful compounds which include methyl p-hydroxyphenyllactate (MeHPLA), its analogues, chemical derivatives and chemically related compounds as antitumor agents and as inhibitors of proliferative cell growth.

BACKGROUND OF THE INVENTION

There are two types of nuclear estrogen binding sites in normal and malignant tissues. Type I sites represent the classical estrogen receptor and nuclear Type II sites appear to mediate a specific nuclear response to estrogenic hormones. After estrogen administration, Type I receptor sites bind estradiol and this receptor-estrogen complex interacts with nuclear acceptor sites before the initiation of the transcriptional events that are associated with estrogen stimulation of tissue growth. In contrast, Type II sites bind estrogen with a higher capacity and a lower affinity than the classical estrogen receptor and do not appear to be translocated from the cytoplasm to the nucleus. Thus, although the levels of nuclear Type II sites are increased by estrogen administration, Type II sites remain in the cytoplasm after hormone administration. Nuclear Type II sites appear to mediate a specific nuclear response to estrogenic hormones and are highly correlated with uterine cellular hypertrophy and hyperplasia. Additionally, nuclear Type II sites are highly stimulated in malignant tissues such as mouse mammary tumors and human breast cancer. This observation is consistent with the findings that highly proliferative tissue has an increased number of nuclear Type II sites. Because the stimulation of nuclear Type II sites is closely correlated with the stimulation of uterine growth, it has been postulated that the Type II sites are the location for the mechanisms by which estrogens cause uterotropic stimulation. Furthermore, the presence of Type II sites on the nuclear matrix suggests a potential role in the regulation of DNA synthesis.

Nuclear Type II sites are constituents of many, if not all, non-malignant cells. Normally, Type II sites in non-malignant cells are occupied by methyl p-hydroxyphenyllactate (MeHPLA or methyl 3-(4-hydroxyphenyl)-2-hydroxypropionate). When MeHPLA binds to Type II sites, cell growth and proliferation of non-malignant tissues are slowed down or stopped. Conversely, malignant cells metabolize MeHPLA and thus there is insufficient binding to the nuclear Type II sites and the regulation of cell growth and proliferation is lost. Consequently all tumor cell populations examined have very high levels of unbound nuclear Type II sites. These sites should represent targets for the analogues of MeHPLA.

This invention discloses compounds which are not metabolized by malignant cells but which bind to nuclear Type II sites with high affinity. These compounds are very effective inhibitors of tumor cell proliferation and DNA synthesis. Since nuclear Type II sites have been observed in a variety of tumor cells, it is likely that analogues of MeHPLA and chemically related compounds will be effective inhibitors of a broad spectrum of tumors. Consequently, any tumor which contains nuclear Type II sites should respond to treatment with MeHPLA, its analogues, derivatives and chemically related compounds, including cancers of the pancreas, cervix, liver, brain, pituitary, prostate and other organ or tissue sites, as well as other cancers, such as leukemias, lymphomas, stromal myomas and leiomyomas, among others. Since MeHPLA will also block estrogen stimulation of normal cell growth such as that in the rat uterus (Table I), analogues of this compound may also be useful for the treatment of uterine hyperplasia, cervical hyperplasia, endometriosis and benign prostatic hypertrophy. Because non-proliferating non-malignant cells normally have their Type II sites bound with MeHPLA, the effects of the proposed compounds on non-malignant cell populations will be minimal to non-existent. For this reason, MeHPLA, its analogues, derivatives and chemically related compounds are also useful as prophylactic agents in the inhibition and prevention of cancer and non-malignant cell growth.

The precise physiological role of Type II sites is unknown, but inhibition of the nuclear Type II sites is associated with antagonism of uterotropic responses to estrogen. This is true for steroid antagonists such as dexamethasone, progesterone and triphenylethylene derivatives such as nafoxidine and clomiphene. While there is at least one endogenous inhibitor of estradiol binding to nuclear Type II sites, the specific inhibitor for the nuclear Type II sites has not been identified previous to this invention. Furthermore, the inhibitor of the present invention is specific to nuclear Type II sites and does not interfere with estradiol binding to cytoplasmic or nuclear Type I estrogen receptors.

The inhibitor is identified as methyl 3-(4-hydroxyphenyl)-2-hydroxypropionate and is an important regulator of cell growth and proliferation in normal and malignant tissues. The inhibitor is also known as methyl p-hydroxyphenyllactate or MeHPLA. These terms may be used interchangeably. Cell growth inhibition by this compound resides in its ability to interact with the high-affinity nuclear binding sites in normal and malignant cells which may be involved in the regulation of cellular proliferation and DNA synthesis. When MeHPLA is bound to nuclear Type II sites, cell growth and proliferation are inhibited. The endogenous 3-(4-hydroxyphenyl)-2-hydroxypropionic acid inhibits the cell growth much less effectively. This activity correlates with its low binding affinity for nuclear Type II sites.

An additional object of the present invention is a means for the prevention of cancer. Since MeHPLA is a normal constituent of mammalian cells, but metabolized by malignant cells, MeHPLA, structural analogues and chemically related compounds as described herein, which are not metabolized by tumors should be useful in the prevention of malignancy. These compounds should possess little if any side effects, and if taken in a low level maintenance dose should inhibit the proliferation of malignant cells.

Because MePHLA is such a potent inhibitor of cell growth, this compound, as well as its analogues and chemically related compounds were used as potential antitumor agents. The present invention discloses the potent antitumor activity of these compounds.

SUMMARY OF THE INVENTION

An object of the present invention is a treatment for cancer.

An additional object of the present invention is a procedure to inhibit the growth of proliferating cells which include a Type II nuclear estrogen binding site.

A further object of the present invention is a method for inhibiting the growth of estrogen responsive tissues.

An additional object of the present invention is the treatment of human breast cancer, and other malignancies which contain unbound nuclear Type II sites.

Another object of the present invention is the treatment of benign prostatic hyperplasia, cervical hyperplasia, uterine hyperplasia and endometriosis.

Thus, in accomplishing the foregoing objects, there is provided in accordance with one aspect of the present invention a method of treating cancer comprising the step of administering a therapeutic dose of MeHPLA, its analogues, chemical derivatives or chemically related compounds. More specifically the compound is selected from the group consisting of the formulae:

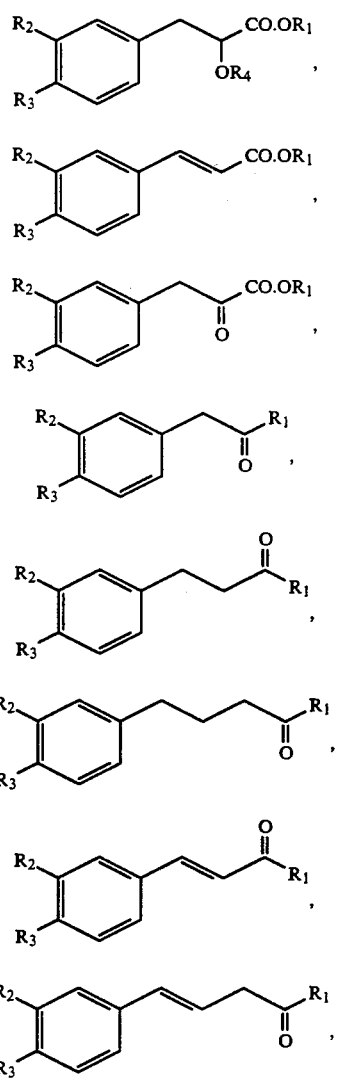

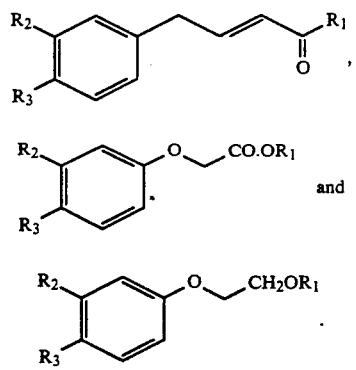

wherein, $R_1$ is selected from the group consisting of H, alkyl groups containing 1 to 6 carbons, and aryl groups; $R_2$ and $R_3$ are selected from the group consisting of H, OH and $OCH_3$ and $R_4$ is selected from the group consisting of H, or alkyl group containing 1 to 6 carbons. Preferred compounds which may be used to practice the present invention may be selected from the group consisting of methyl 3-(4-hydroxyphenyl)-2-hydroxypropionate, n-propyl 3-(4-hydroxyphenyl)-2-hydroxypropionate, n-butyl 3-(4-hydroxyphenyl)-2-hydroxypropionate, 3-(4-hydroxyphenyl)-2-propenoic acid, 4-(4-hydroxyphenyl)-2-butanone, 1-(4-hydroxyphenyl)-3-pentanone, methyl (4-hydroxyphenoxy)acetate, and methyl 3-(3,4-dihydroxyphenyl)-2-propenoate.

Another aspect of the invention involves the inhibition of the growth of proliferating cells which include a Type II nuclear estrogen binding site by the step of administering a biological inhibiting dose of MeHPLA, its analogues, chemical derivatives or chemically related compounds to the proliferating cells.

An additional aspect of the present invention is the inhibition of the proliferative growth of estrogen responsive tissues such as uterus, mammary gland, uterine tumors and mammary tumors. In one specific aspect, the above-mentioned compounds have been used for the treatment of human breast cancer cells. The compounds inhibit the growth of human breast cancer cells.

Another specific aspect of the present invention is a method for treating benign prostatic hyperplasia comprising the step of administering a therapeutic dose of MeHPLA, its analogues, chemical derivatives or chemically related compounds.

Another aspect of the present invention is provision of an antitumor agent which comprises MeHPLA, its analogues, chemical derivatives or chemically related compounds.

Another aspect of the present invention is prophylactic agents to inhibit and prevent cancer and non-malignant cell growth. These prophylactic agents include the above-mentioned MeHPLA, its analogues, chemical derivatives or chemically related compounds.

Other and further objects, features and advantages will be apparent from the following description of the presently preferred embodiments of the invention given for the purpose of disclosure.

DETAILED DESCRIPTION OF THE SPECIFIC EMBODIMENT DEFINITIONS

Figure 1A:
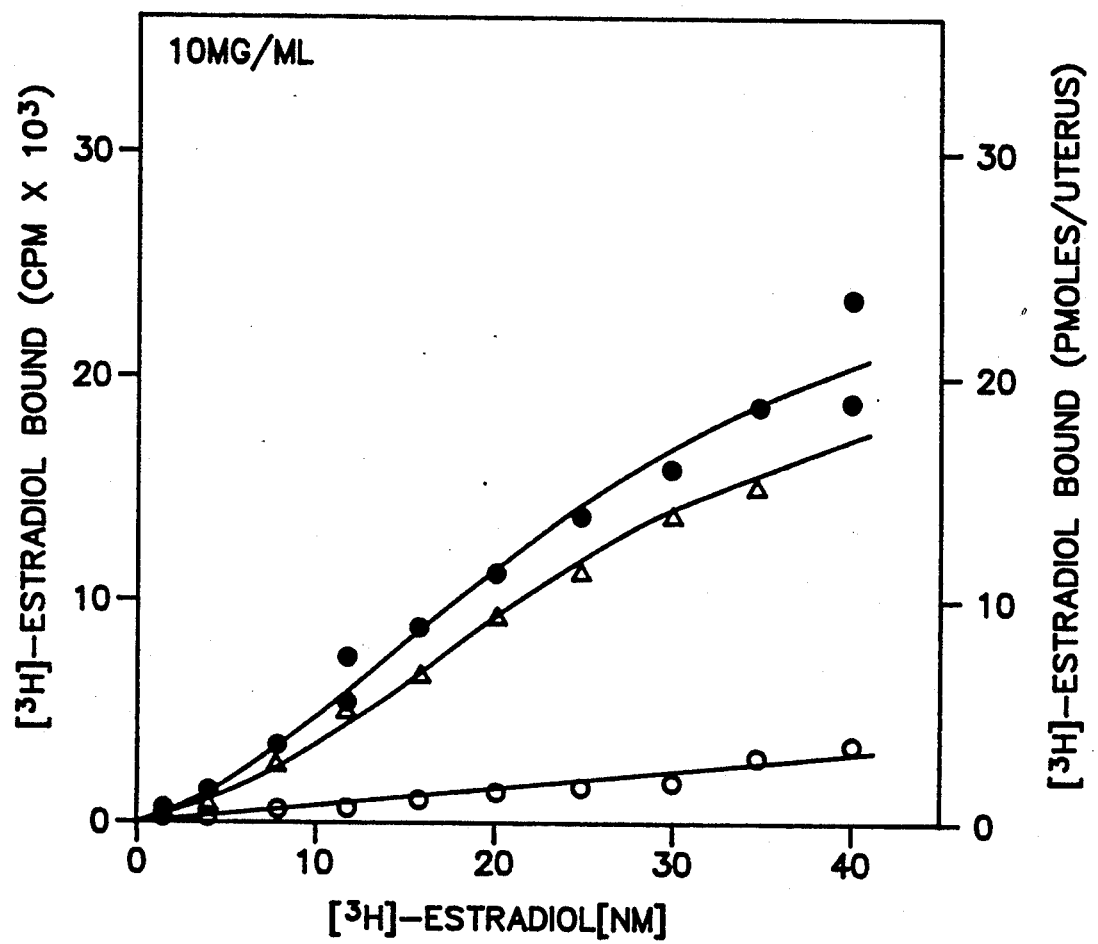
FIG. 1 demonstrates the effect of dilution on [$^3$H]estradiol binding in uterine nuclear fractions from estradiol-17$\beta$ implanted adult ovariectomized rats.
Figure 1B:
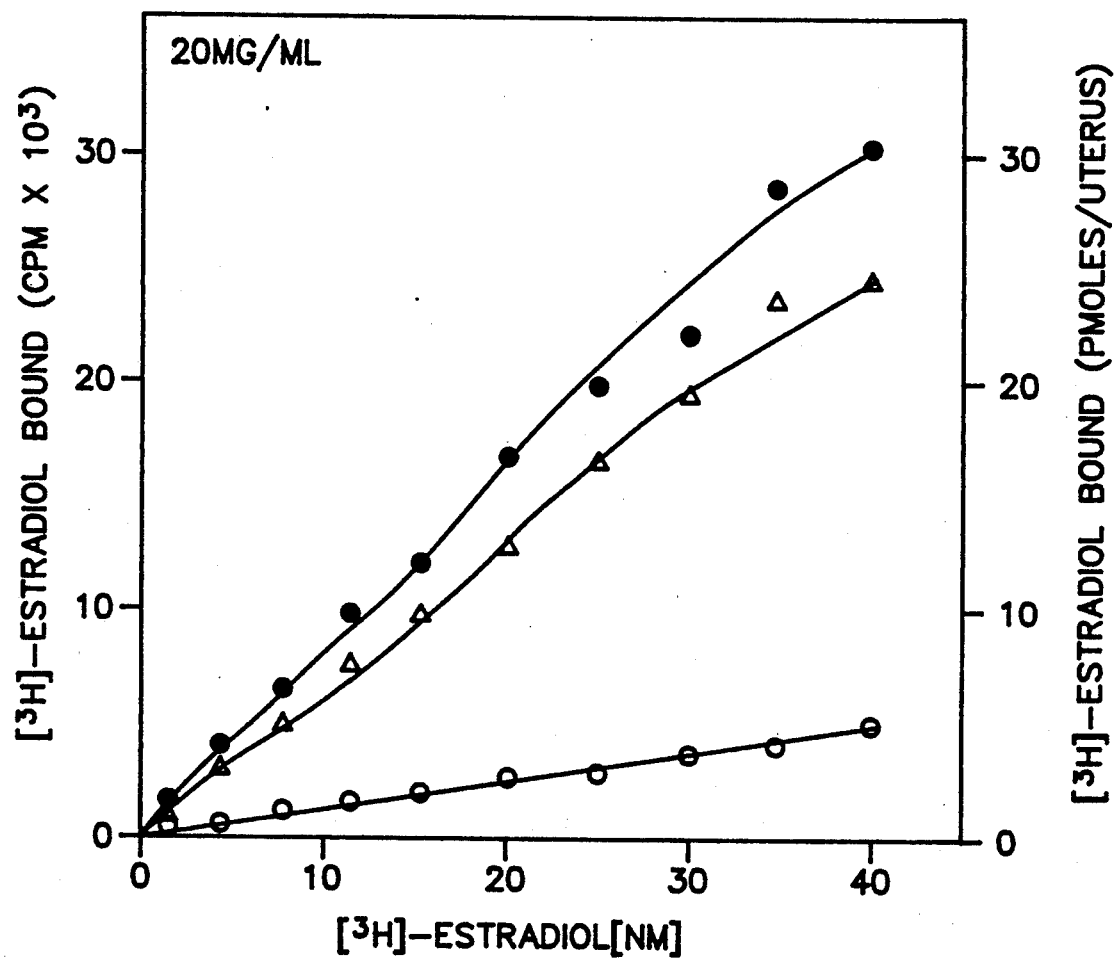
Figure 1C:
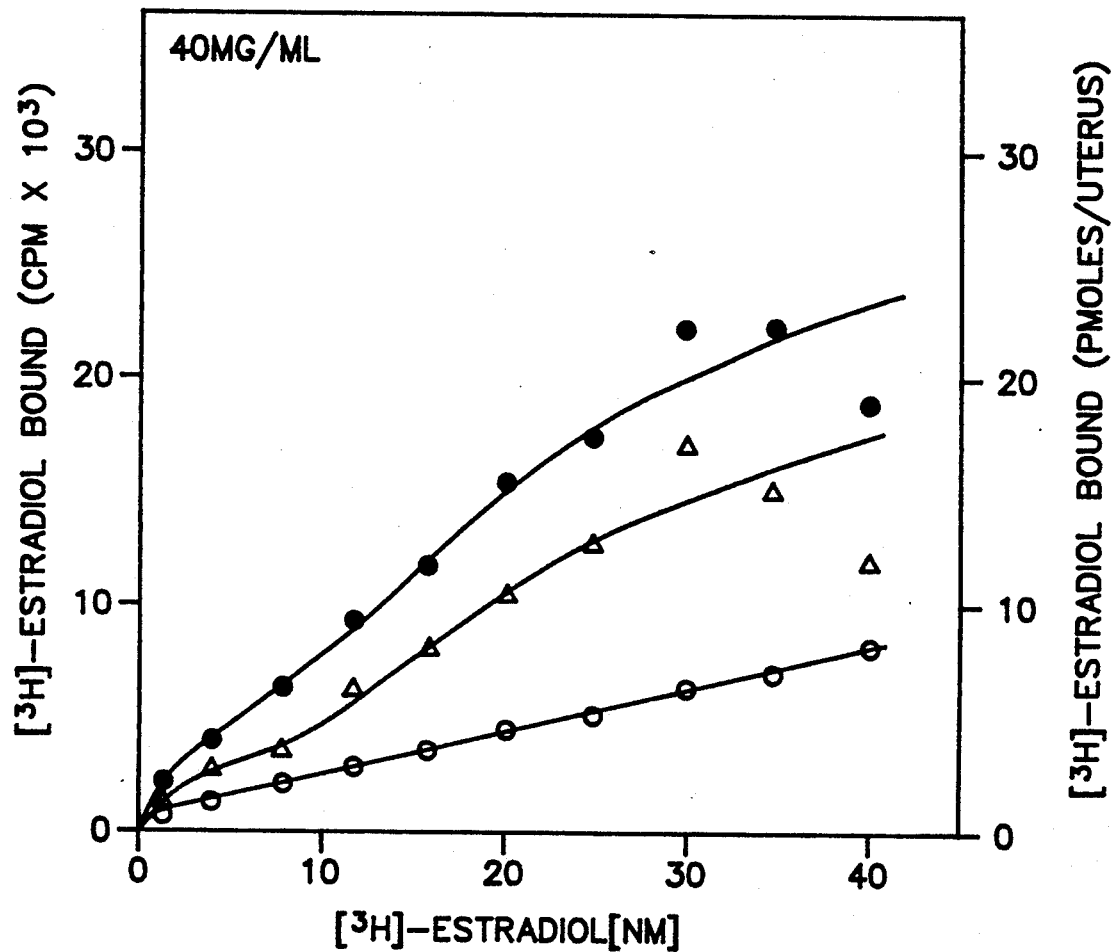
Figure 1D:
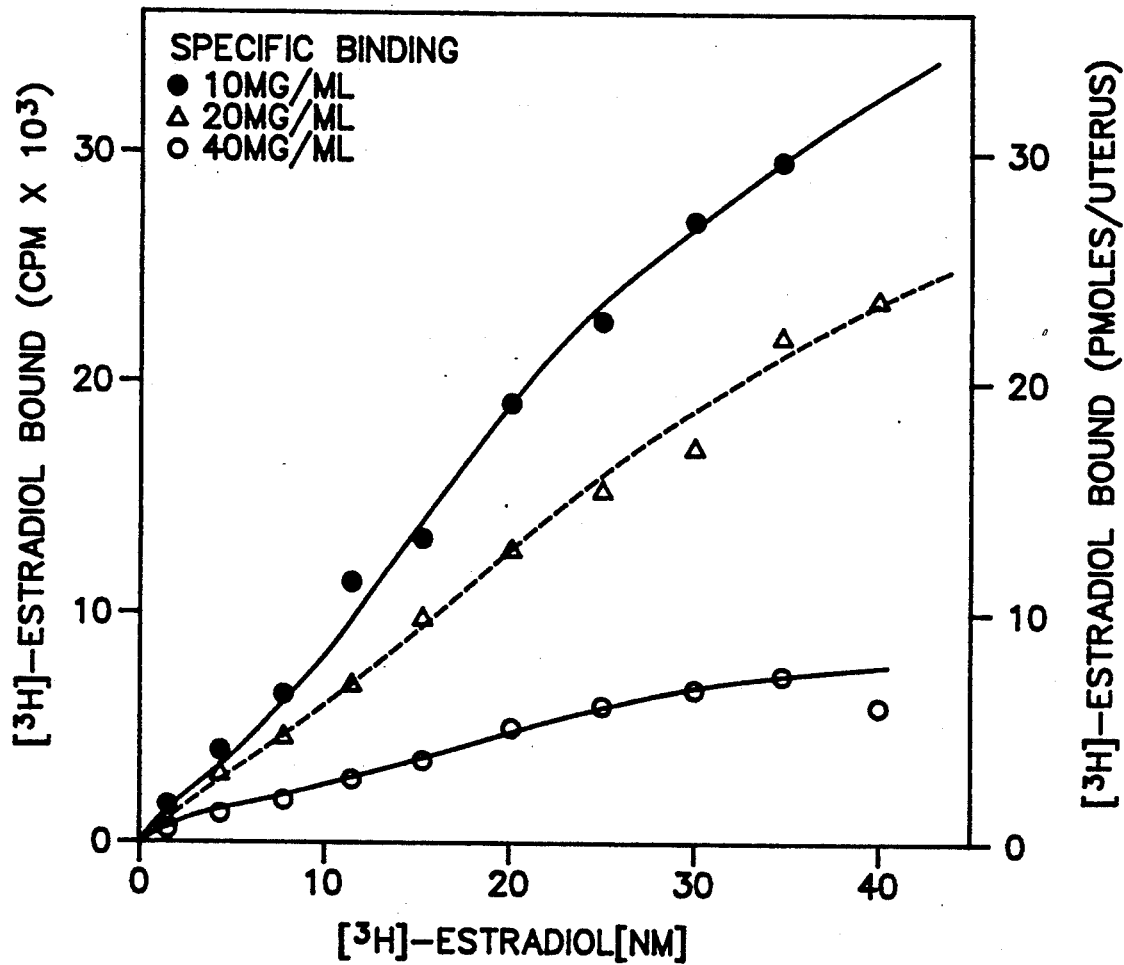

"Methyl 3-(4-hydroxyphenyl)-2-hydroxypropionate" is also known as methyl p-hydroxyphenyllactate of MeHPLA. The term "MeHPLA" is meant to also include its analogues, chemical derivatives, and chemically related compounds which bind to the nuclear Type II receptors and by so doing inhibit cell proliferation.

The term "chemically related compounds" refers to the derivatives and analogues of p-coumaric acid, p-hydroxyphenylbutanone, (4-hydroxyphenoxy)acetate and the arylpropenaldehydes, alkyl arylethenyl ketones, aryl arylethenyl ketones, aryl butenaldehydes, alkyl arylpropenyl ketones and arylpropenyl ketones which are structurally related to MeHPLA and disclosed herein. These chemically related compounds include the cis and trans isomers of said compounds and their esters, ethers, ketones and derivatives containing S or N in place of O atoms. More specifically these structurally related analogues and derivatives include compounds where $R_1$ represents the methyl, ethyl, n-propyl, n-butyl, isopropyl, tert-butyl or aryl group and $R_2$ and $R_3$ represent H, OH or OCH$_3$ groups and $R_4$ is H or an alkyl group of 1 to 6 carbons. Specific analogues of each class of these structurally related compounds to MeHPLA have been demonstrated to possess biological activity (Table I) as defined herein and therefore mimic MeHPLA as an effective inhibitor of cell proliferation and tumor cell growth.

The term "individual" is meant to include animals and humans.

The term "biologically inhibiting" or "inhibition" of the growth of proliferating cells is meant to include partial or total growth inhibition and also is meant to include decreases in the rate of proliferation or growth of the cells. The biologically inhibitory dose of the compounds of the present invention may be determined by assessing the effects of the test compound on malignant cell growth in tissue culture (see FIG. 12), uterine growth in the animal (see FIGS. 14 and 15) or tumor growth in the animal as previously described by Markaverich et al., Cancer Research 43:3208–3211 (1983), or any other method known to those of ordinary skill in the art.

The term "prophylactic agent" is meant to include agents which may be used for partial or total inhibition or prevention of disease and the spread of disease and also is meant to include agents which may be used as a precaution against disease and for preventive treatment of disease.

Administration of the compounds useful in the method of the present invention may be by topical, parenteral, oral, intranasal, intravenous, intramuscular, subcutaneous, or any other suitable means. The dosage administered is dependent upon the age, weight, kind of concurrent treatment, if any, and nature of the malignancy. The effective compound useful in the method of the present invention may be employed in such forms as capsules, tablets, liquid solutions, suspensions, or elixirs, for oral administration, or sterile liquid forms such as solutions, suspensions or emulsions. Any inert carrier is preferably used, such as saline, or phosphate-buffered saline, or any such carrier in which the compounds used in the method of the present invention have suitable solubility properties.

The compounds of the present invention may be administered in a biologically effective carrier. The biologically effective carriers may include any solvent with which the compounds of the present invention are compatible and which are non-toxic to the individuals treated at the amounts administered.

The term "antitumor agent" is meant to include agents which decrease cell growth, or inhibit the proliferation of tumor cells when administered to said tumor cells in an effective dose.

One specific embodiment of this invention is an antitumor agent including MeHPLA, its analogues, chemical derivatives or chemically related compounds. Specific examples of MeHPLA analogues are derivatives of the general formula

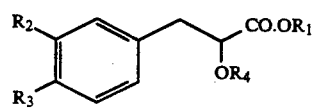

One specific example of this type of compound is methyl 3-(4-hydroxyphenyl)-2-hydroxypropionate wherein $R_1$ is CH$_3$, $R_2$ is H, $R_3$ is OH and $R_4$ is H. This is a naturally occurring endogenous compound which was isolated and characterized and identified as the present invention. Other examples of analogues include the compounds in which the $R_1$ group has been replaced by an ethyl, n-propyl, n-butyl, isopropyl, tert-butyl or aryl group; $R_2$ and/or $R_3$ have been replaced with an H, OH or $OCH_3$ group and $R_4$ is H or an alkyl group of 1 to 6 carbons. Each of these esters can exist in the D and L form.

Another group of derivative compounds includes those with the formula:

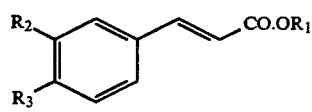

Examples of these compounds are p-coumaric acid, 3-(4-hydroxyphenyl)-2-propenoic acid, and its esters. These substances exist as cis and trans isomers. In coumaric acid $R_1$ and $R_2$ are hydrogen and $R_3$ is OH. Additional esters include compounds wherein $R_1$ is methyl, ethyl, n-propyl, n-butyl, isopropyl, tert-butyl or aryl and $R_2$ and/or $R_3$ is a H, OH or $OCH_3$ group. Additional analogues include caffeic acid, 3-(3,4-dihydroxyphenyl)-2-propenoic acid, wherein $R_1$ is H and $R_2$ and $R_3$ are both OH. Additionally the methoxy compound is very effective as an antitumor agent.

Other compounds with antitumor activity are the derivatives of 1-(4-hydroxyphenyl)-3-butanone, such as compounds with the formulae:

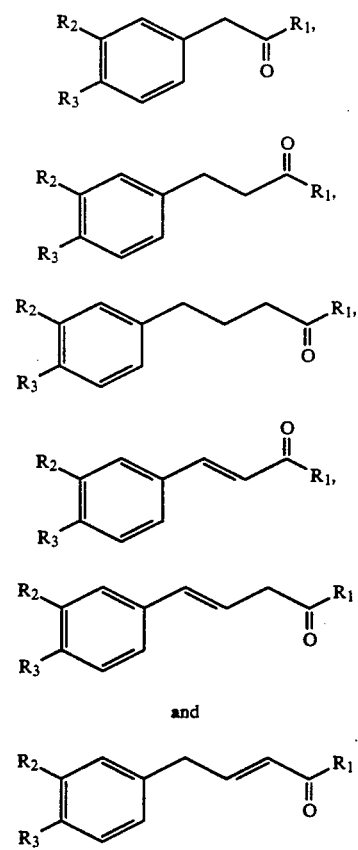

and

Ketone derivatives include compounds with a methyl, ethyl, n-propyl, n-butyl, isopropyl, tert-butyl or aryl group at the $R_1$ position, H, OH or $OCH_3$ group at the $R_2$ and $R_3$ positions; and most preferably H at the $R_2$ position and OH at the $R_3$ position.

Additionally, as can be seen by the formulae, the number of $CH_2$ groups between the aromatic entity and the keto group can be varied. Specific examples of compounds are 1-(4-hydroxyphenyl)-3-pentanone and 1-(4-hydroxyphenyl)-3-butanone. These compounds have been shown to bind to Type II sites and to have antitumor proliferative activity in the uterotropic assay.

Another group of compounds which show antitumor proliferative activity in the rat uterus is described by the formula:

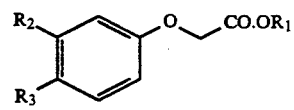

These compounds are ether-linked analogues of (4-hydroxyphenoxy)acetic acid, for example, methyl (4-hydroxyphenoxy)acetate. All of these compounds bind to the Type II binding sites. These ether-linked compounds include analogues wherein $R_1$ is H, a $C_1$ to $C_6$ alkyl carbon chain or an aryl group, $R_2$ and $R_3$ are H, OH or $OCH_3$. An additional variation on the phenoxy compounds include the ether compounds, for example, 2-(4-hydroxyphenoxy)ethyl methyl ether, wherein $R_1$ can be H or any $C_1$ to $C_6$ alkyl carbon chain or an aryl group, $R_2$ and $R_3$ are H, OH or $OCH_3$ in the formula:

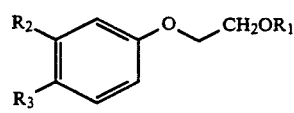

Additionally useful is the compound of the formula:

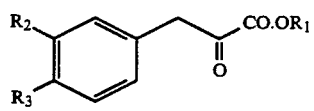

wherein $R_1$ is a $C_1$ to $C_6$ alkyl chain or an aryl group, $R_2$ and $R_3$ are H, OH or $OCH_3$.

Another group of compounds which show tumor anti-proliferative action is described by the general formulas:

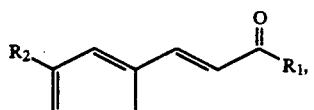

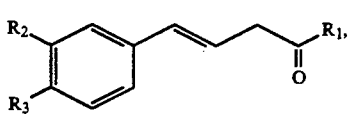

and

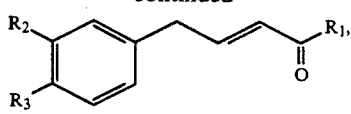

wherein $R_1$ is from the group consisting of H, alkyl groups containing 1 to 6 carbons, and substituted or unsubstituted aryl groups; and $R_2$ and $R_3$ are selected from the group consisting of H, OH and $OCH_3$. Preferred compounds of this group which may be used to practice the present invention are:

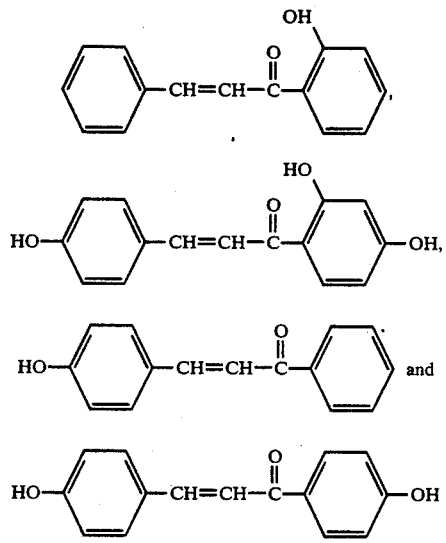

Most preferred compounds of this group for practicing the present invention are 3-(4-Hydroxyphenyl)-1-phenyl-2-propen-1-one and 4-(4-Hydroxyphenyl)-3-buten-2-one, analogs, chemical derivatives and chemically related compounds and pharmaceutically acceptable salts thereof. Another embodiment of the present invention includes a method for treating cancer comprising the step of administering a therapeutic dose of MeH-PLA, its analogues, chemical derivatives or chemically related compounds. This compound, can be any of the above-described antitumor compounds.

In addition to being used as a treatment for cancer, these antitumor agents are also useful as inhibitors of cell growth and proliferation in those cells which include a Type II nuclear estrogen binding site. These compounds bind to Type II nuclear estrogen binding sites and regulate cell growth. Specific proliferating cells which are sensitive to the binding of these compounds include estrogen responsive tissues such as uterus, mammary gland, uterine tumors and mammary tumors. The above-described compounds inhibit the proliferative capacity of human breast cancer cells and thus provide an effective therapy for this disease.

Benign prostatic hyperplasia is another example of a proliferative tissue disease in which the above-described compounds can successfully be used in the treatment.

Binding Assay

Tissue was dissected from host animals, weighed, rinsed in saline, and homogenized in 10 mM Tris-1.5 mM EDTA, by approximately four 30-sec bursts in a Sorval Omnimixer with intermittent cooling for about 5 min. This crude homogenate was transferred to a Kontes ground glass homogenizer and further homogenized with intermittent cooling until no tissue aggregates were visible. It was imperative that the homogenate be kept cold, about 4° C. through all homogenization steps. The final homogenate was centrifuged at $800 \times g$ for approximately 20 min to obtain the crude nuclear pellet, which was then washed by gentle resuspension in a Dounce homogenizer and then centrifuged at $800 \times g$ for approximately 7 min. The final washed nuclear pellet was resuspended in 10 mM Tris-1.5 mM EDTA in a concentration ranging from 5 to 50 mg of fresh tissue equivalents/ml. By the term "fresh tissue equivalent" is meant the amount of material which represents the initial concentration in the fresh uterine tissue.

To assess total and nonspecific binding, aliquots of the nuclear suspension were incubated at 37° C. for 30 min with various concentrations ranging from 2 to 40 nM of [$^3$H]estradiol with and without a large molar excess of diethylstilbestrol. The diethylstibestrol concentration ranged from 0.6 to 12.0 $\mu$M. Following incubation, the nuclear pellets were resuspended in about 1 ml of 10 mM Tris-1.5 mM EDTA buffer and centrifuged at $800 \times g$ for about 7 min. The pellet was extracted with 1 ml of ethanol at about 30° C. for about 30 min, and counted in 4 ml of Liquifluor. Specific binding was determined by substraction of nonspecific binding; i.e., not competable by diethylstilbestrol from the total quantity of [$^3$H]estradiol bound. Results were expressed as sites/cell, assuming 8 pg of DNA/cell nucleus and that each binding site binds one molecule of [$^3$H]estradiol.

Inhibition Assay

A variety of rat tissues possess an endogenous ligand which blocks [$^3$H]estradiol binding to nuclear Type II estrogen binding sites; however, this compound does not interfere with [$^3$H]estradiol binding to the estrogen receptor. In order to assess the levels of this inhibitor activity in various tissue cytosols and LH-20 column chromatography fractions from these cytosols, the following inhibition assay was used. Uterine nuclei were prepared from estrogen-implanted, adult-ovariectomized rats. The washed nuclear pellet was diluted to 10 mg of fresh uterine equivalents/ml. At this concentration the effects of the endogenous inhibitor were minimal, and nuclear Type II sites bound maximum quantities of [$^3$H]estradiol. Aliquots of these nuclei and the inhibitor sample were incubated at about 4° C. for approximately 60 min in the presence of 40 nM of [$^3$H]estradiol with and without 12 $\mu$M diethylstilbestrol. Under these conditions, nuclear Type II sites were quantitatively measured without interference from Type I sites. The nuclear pellets were resuspended in 1 ml of 10 mM Tris-1.5 mM EDTA and centrifuged, ethanol extracted, and counted. The results were expressed as the percentage of [$^3$H]estradiol bound as compared to the buffer control, or as the percentage of inhibition where 100% bound was 0% inhibition and was equivalent to approximately 45,000 cpm.

Figure 2:
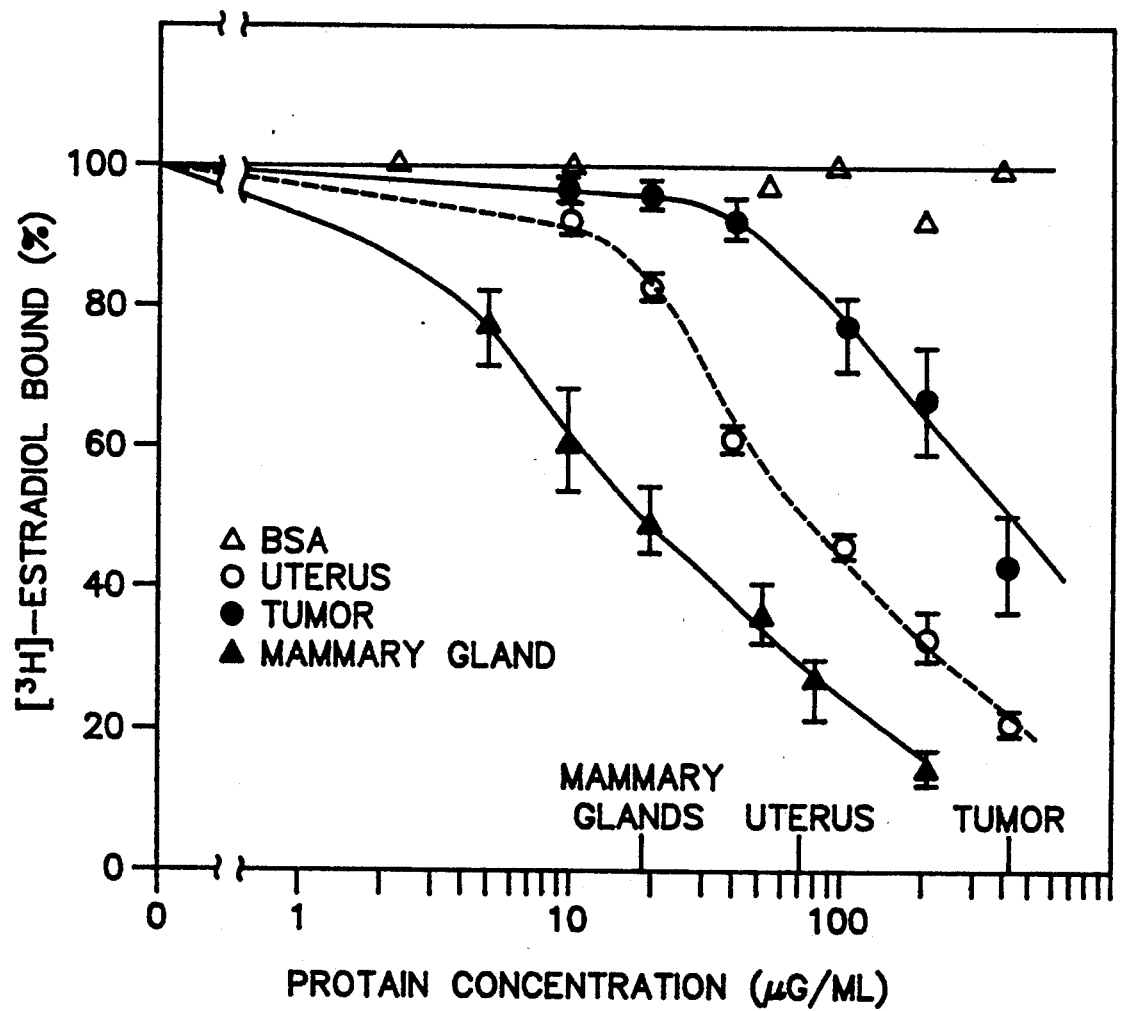
FIG. 2 demonstrates that tumor cytosol preparations contain lower levels of inhibitor activity for nuclear Type II site, than cytosol preparations from uterus or mammary gland.
Figure 3A:
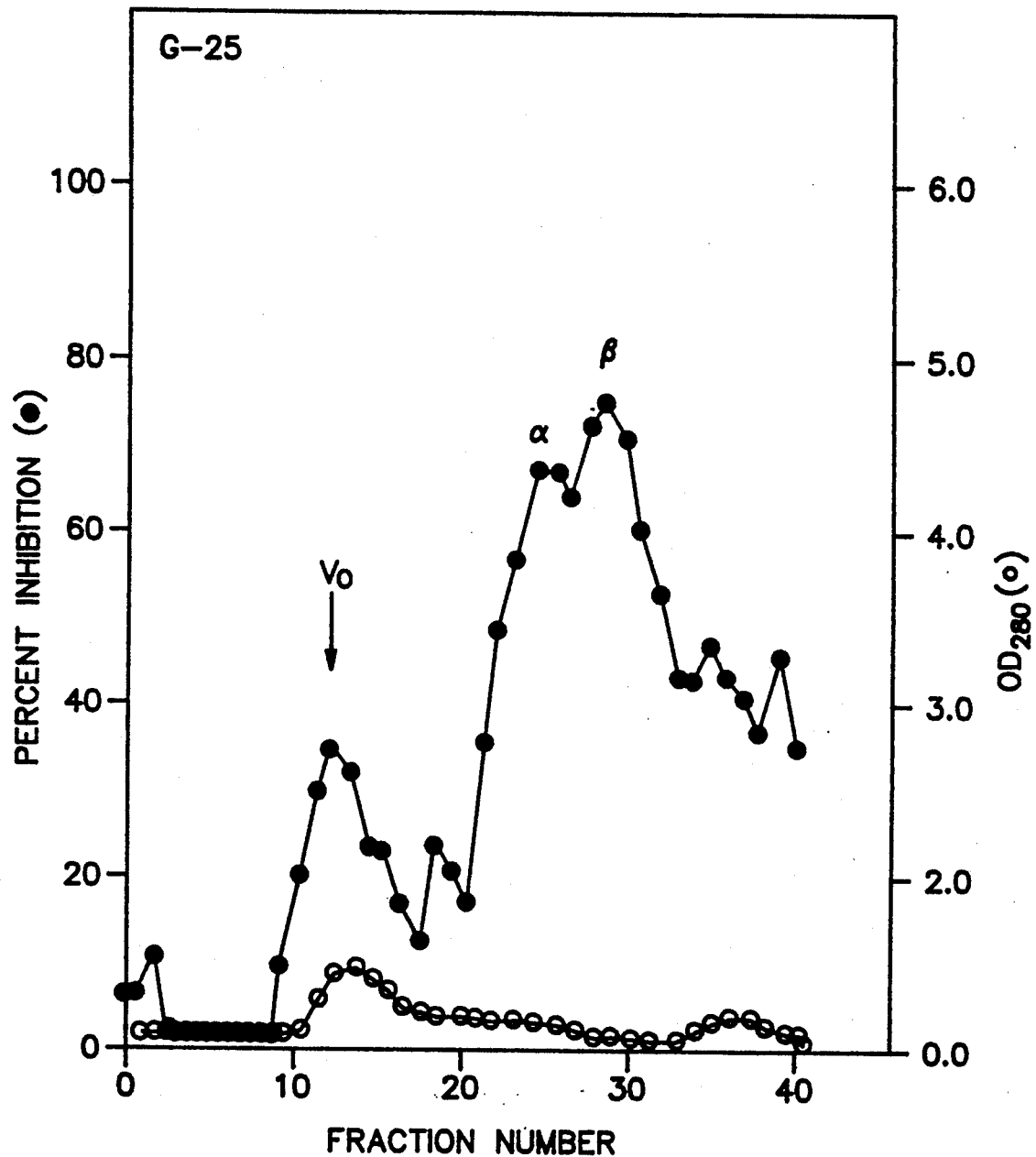
FIG. 3 shows the chromatographic profile of rat uterine cytosol inhibitor preparations on Sephadex G-25 (panels A, C, and D) or LH-20 (panel B) columns.
Figure 3B:
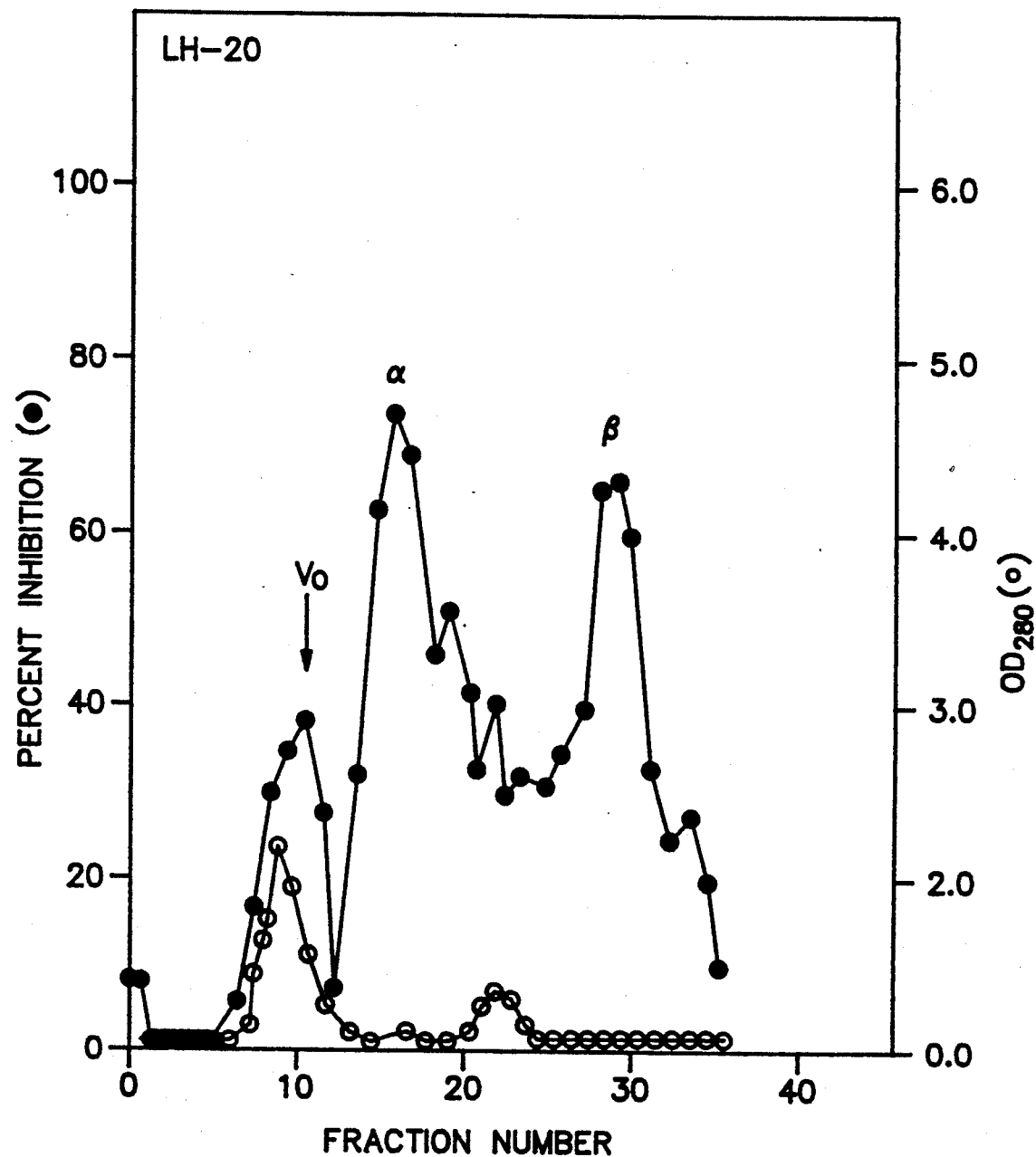
Figure 3C:
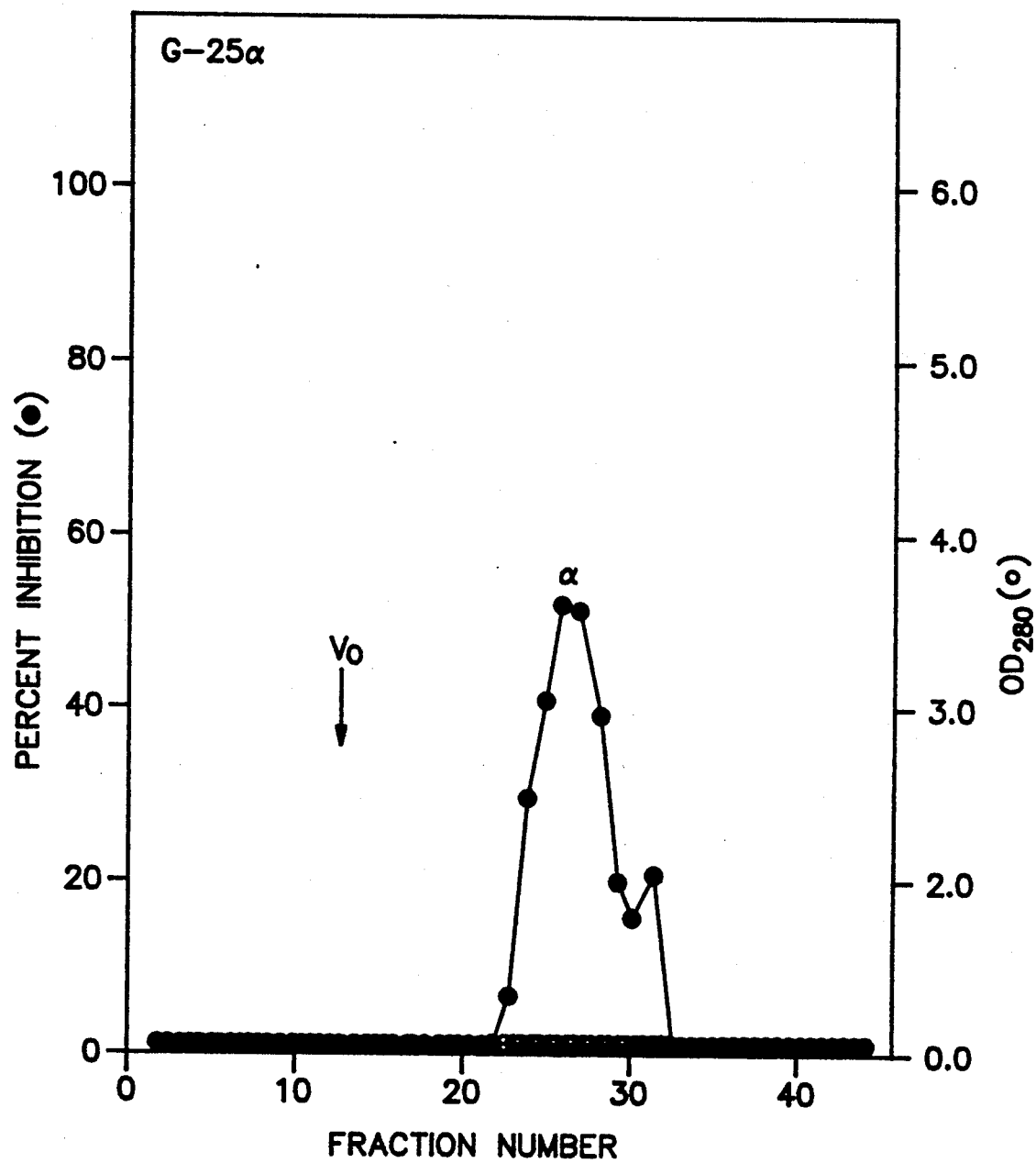
Figure 3D:
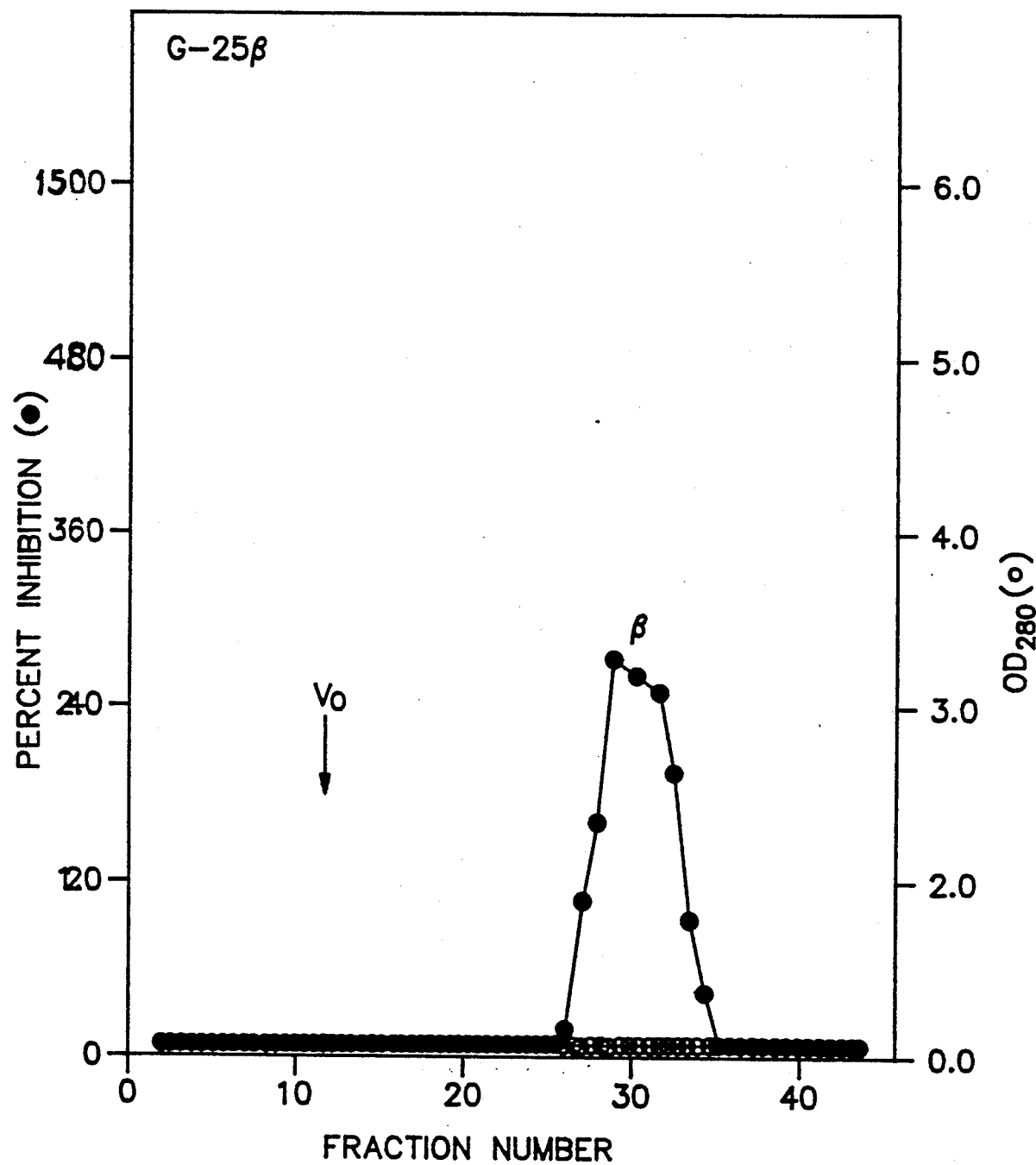

The numbers of nuclear Type II sites measured in the binding assay increased significantly, four-to eight-fold, with nuclear dilution. Thus, more nuclear Type II sites are measured in dilute than in concentrated nuclei. FIG. 1 shows the effects of the dilution on [$^3$H]estradiol binding in uterine nuclear fractions from estradiol-17$\beta$ implanted adult ovariectomized rats. The uterine nuclei were prepared as previously described in Markaverich, B. M. et al., J. Biol. Chem. 258:11663-11671 (1983), the disclosure of which is herein incorporated by reference. Briefly, uterine nuclei after preparation were diluted in 10 mM Tris, 1.5 mM EDTA buffer in final volumes equivalent to 10, 20 or 40 mg fresh uterine equivalents per ml, and assayed for estrogen binding sites by [$^3$H]estradiol exchange at 37° C. for 30 minutes. Specific binding was determined by subtraction of non-specific binding, i.e., non-competable with 300-fold excess diethylstilbestrol, from the total quantity of [$^3$H]estradiol bound. The results shown in FIG. 1, panel D demonstrate the specific binding measured at 10, 20 or 40 mg nuclear equivalents per ml corrected for the dilution effect (pmoles/uterus). These results suggest that rat uterine nuclear preparations contain a factor which inhibits [$^3$H]estradiol binding to nuclear Type II sites and that the interaction of this factor with Type II sites is decreased by dilution. Using an "inhibition assay" it was found that rat uterine cytosol contained a factor which inhibits [$^3$H]estradiol binding to nuclear Type II sites. Briefly, acid-precipitated, boiled cytosol from rat uterus, mouse mammary tumor and normal mouse mammary gland was diluted as shown on FIG. 2 and evaluated for inhibitor activity. FIG. 2 shows that this factor is very effective and completely inhibits the Type II site at very dilute cytosol concentrations. The results represented by FIG. 2 represent the mean±standard error of the mean for triplicate determinations in four replicate experiments for each preparation. This inhibitor activity was stable to acid and was not destroyed by trypsin, proteinase K, RNAse or DNAse.

The inhibitor responsible for this activity was characterized as methyl 3-(4-hydroxyphenyl)-2-hydroxypropionate. The identification and characterization procedure involved chromatography of cytosol preparations on Sephadex G-25 and Sephadex LH-20 columns (FIG. 3). Column fractions were assayed for inhibitory activity by incubating with dilute nuclear fractions from estradiol implanted rats. Under these conditions maximum [$^3$H]estradiol binding to nuclear Type II sites was observed in the absence of inhibitor activity. Sephadex G-25 chromatography resulted in two major peaks ($\alpha$ and $\beta$) of inhibitor activity eluting in the inclusion volume of the column. Chromatography of the same cytosol preparation on Sephadex LH-20 also revealed two peaks showing inhibitor activity. When the LH-20 peaks were individually rechromatographed on the Sephadex G-25, the LH-20 $\alpha$ and $\beta$ peaks eluted in positions identical to the components previously seen on the Sephadex G-25. Further characterization of the compounds with the inhibition assay demonstrated that the $\beta$ compound was much more inhibitory than was the $\alpha$ component and thus is a preferred compound for use in cell growth regulation.

Figure 4:
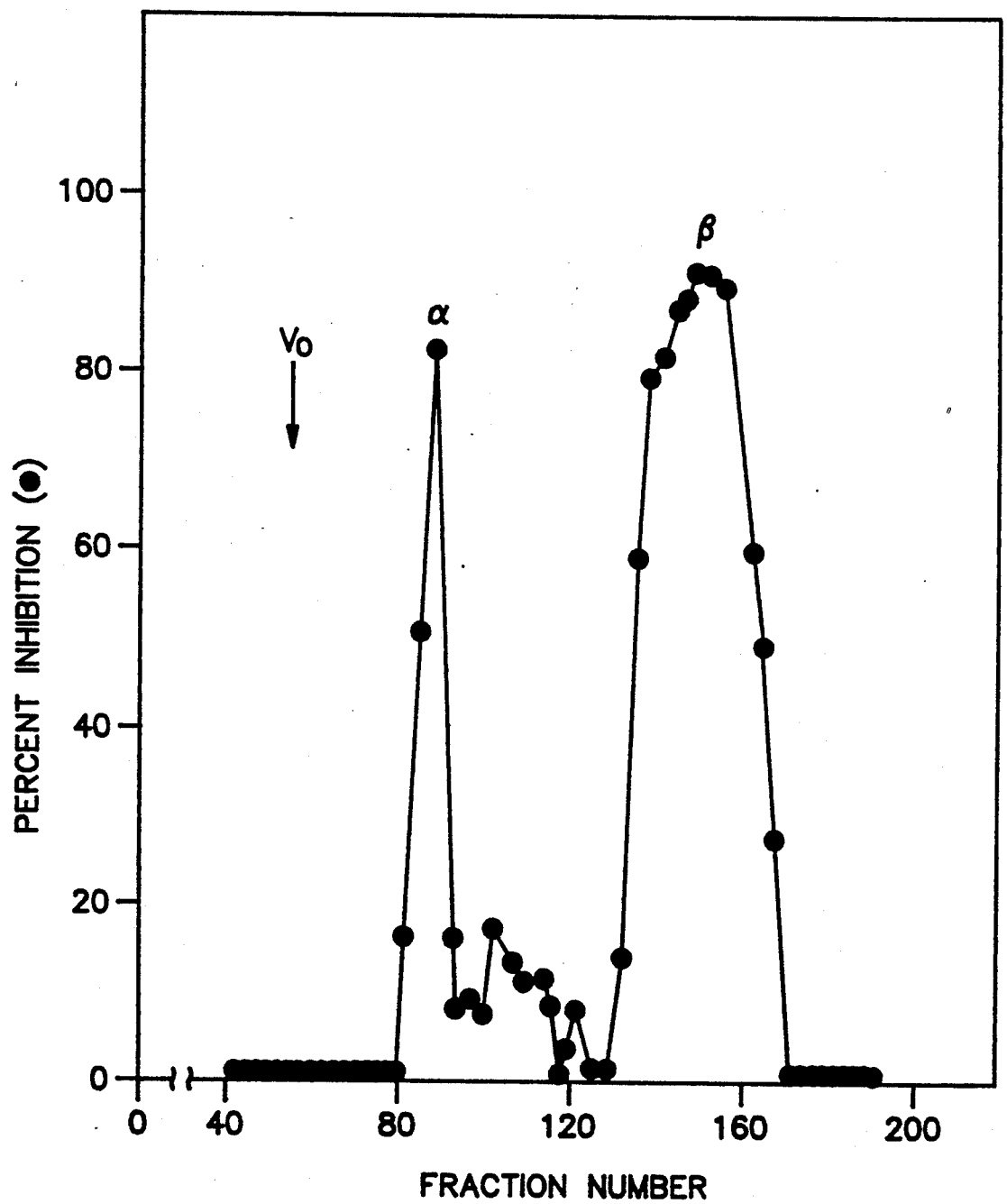
FIG. 4 demonstrates the chromatographic profile of bovine serum extract on a preparative LH-20 column.
Figure 5A:
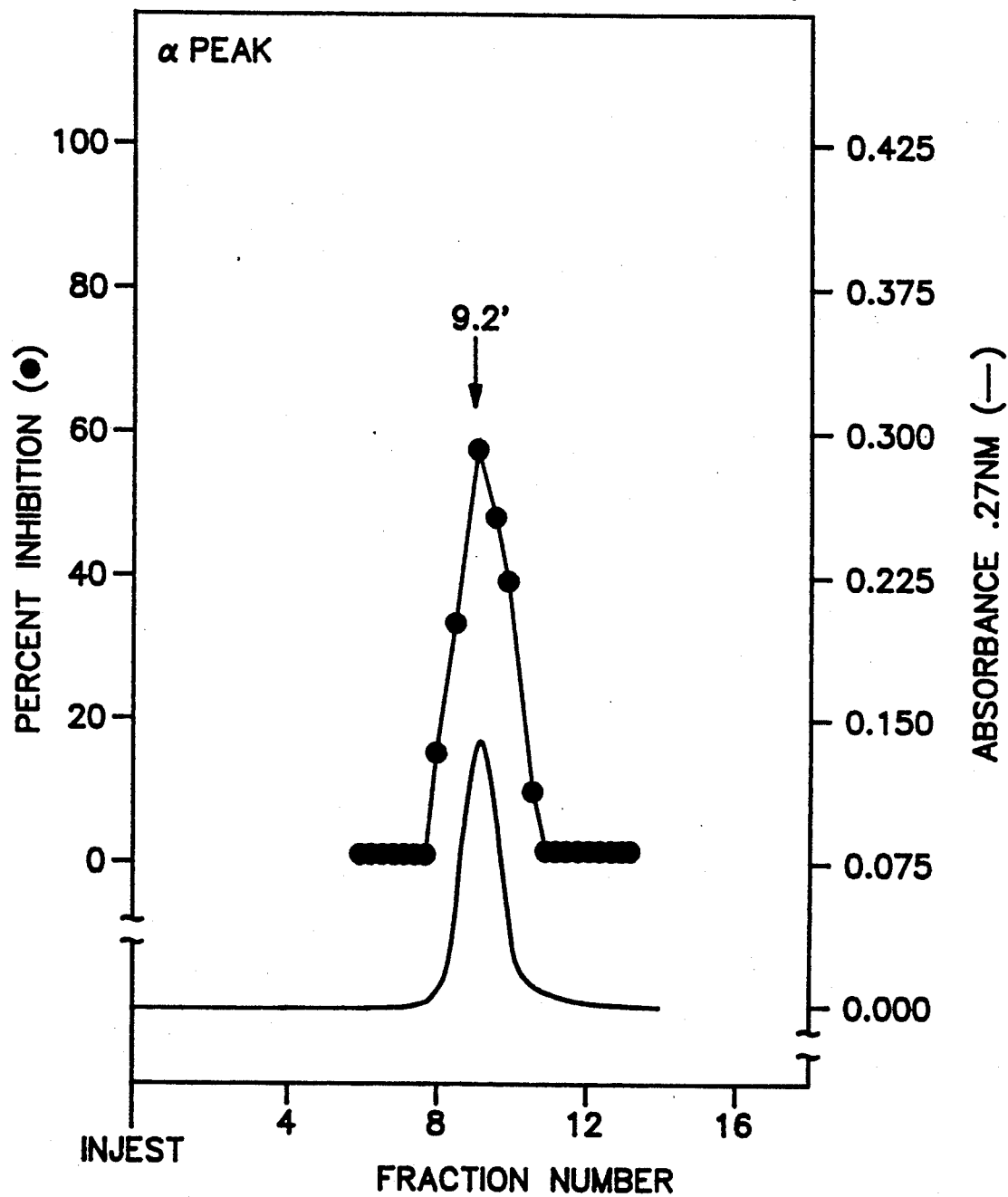
FIG. 5 demonstrates the chromatographic profile of α and β Type II ligand by HPLC.
Figure 5B:
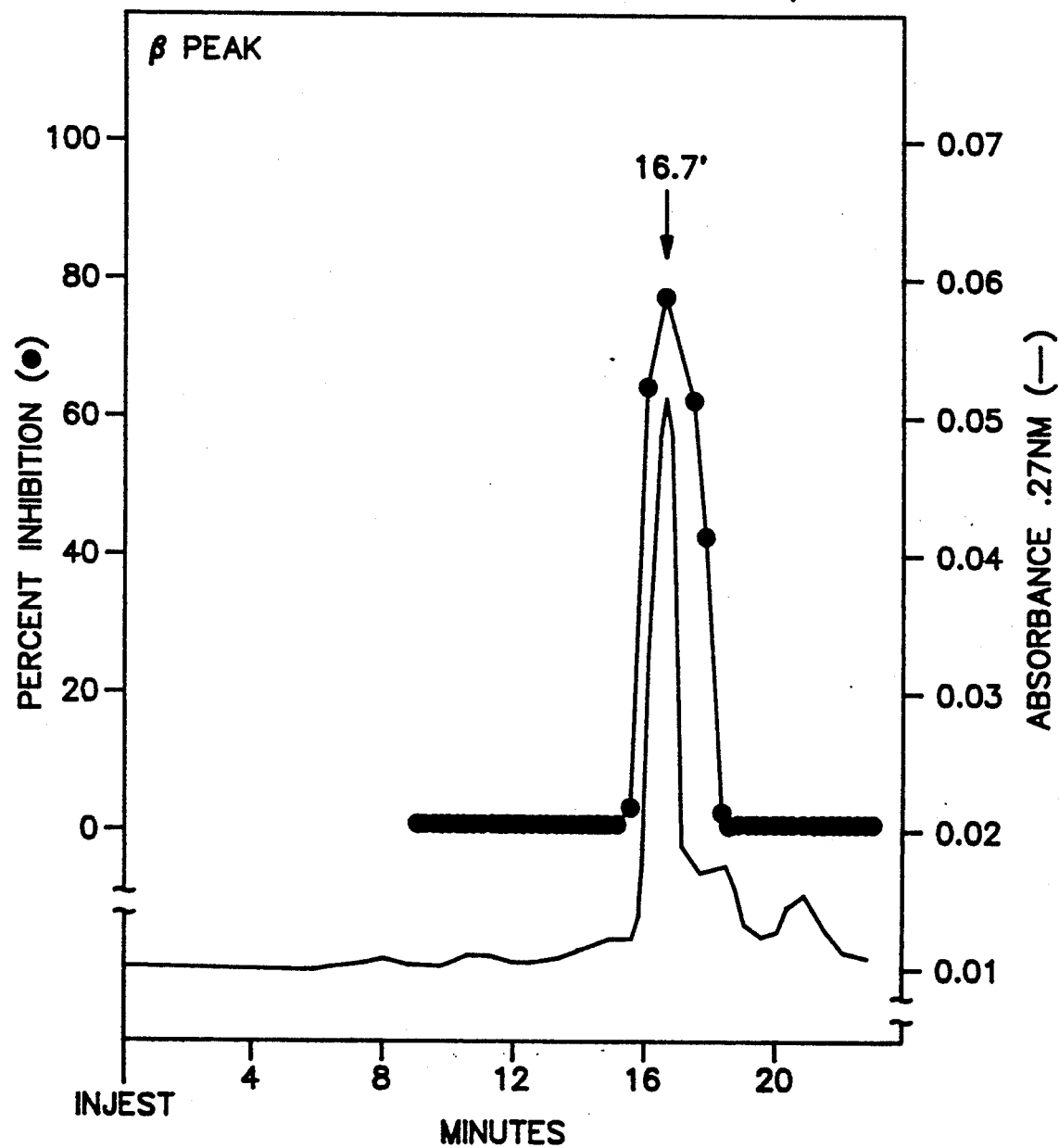
Figure 6A:
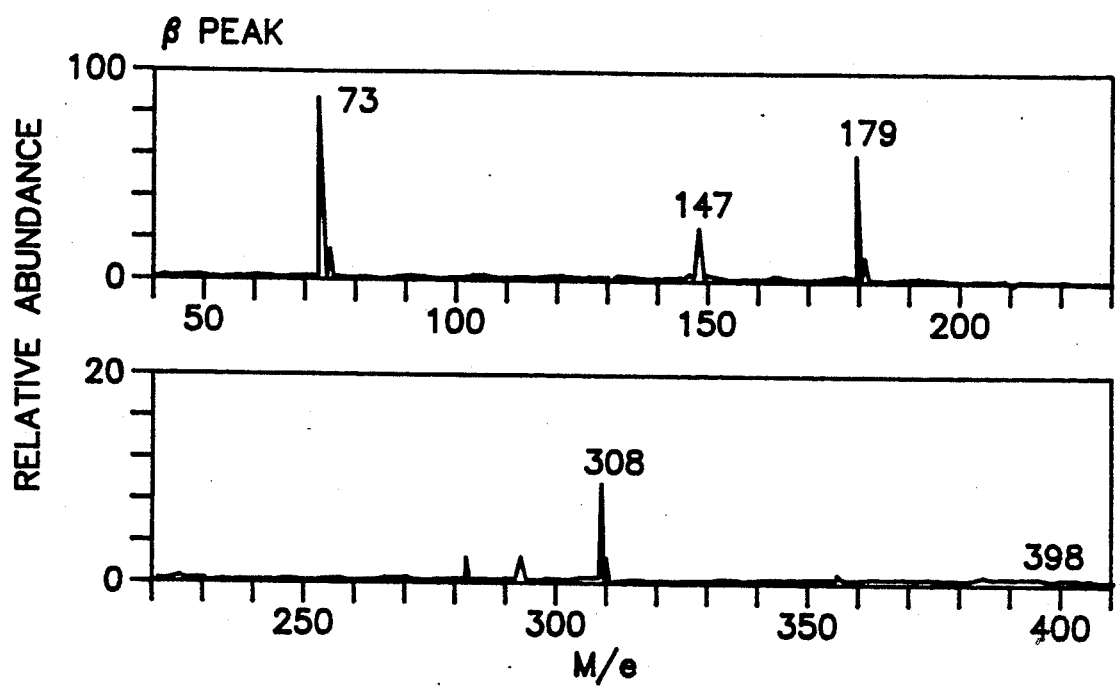
FIG. 6 demonstrates the mass spectra of the trimethylsilyl derivatives of the α peak (A) purified from fetal bovine serum and authentic p-hydroxyphenyllactic acid (B;HPLA).
Figure 6B:
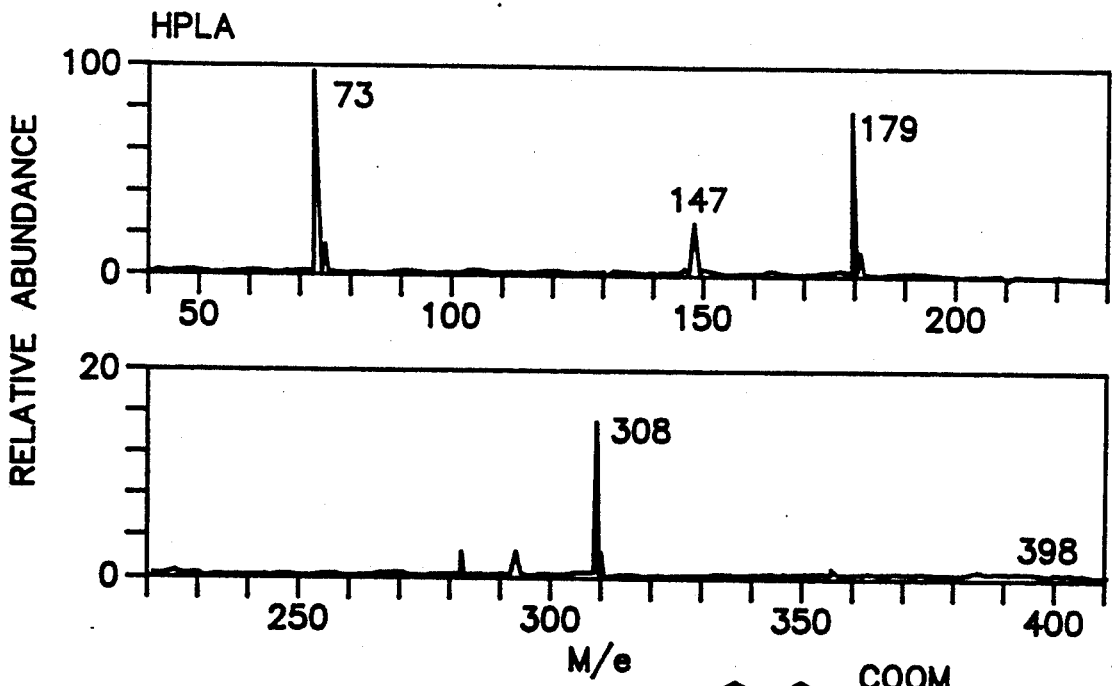
Figure 6B:
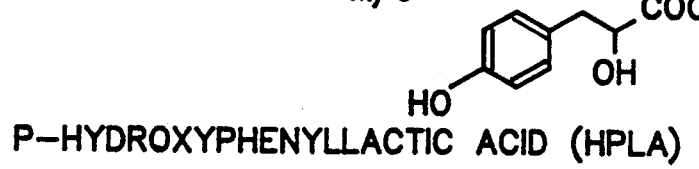
Figure 7A:
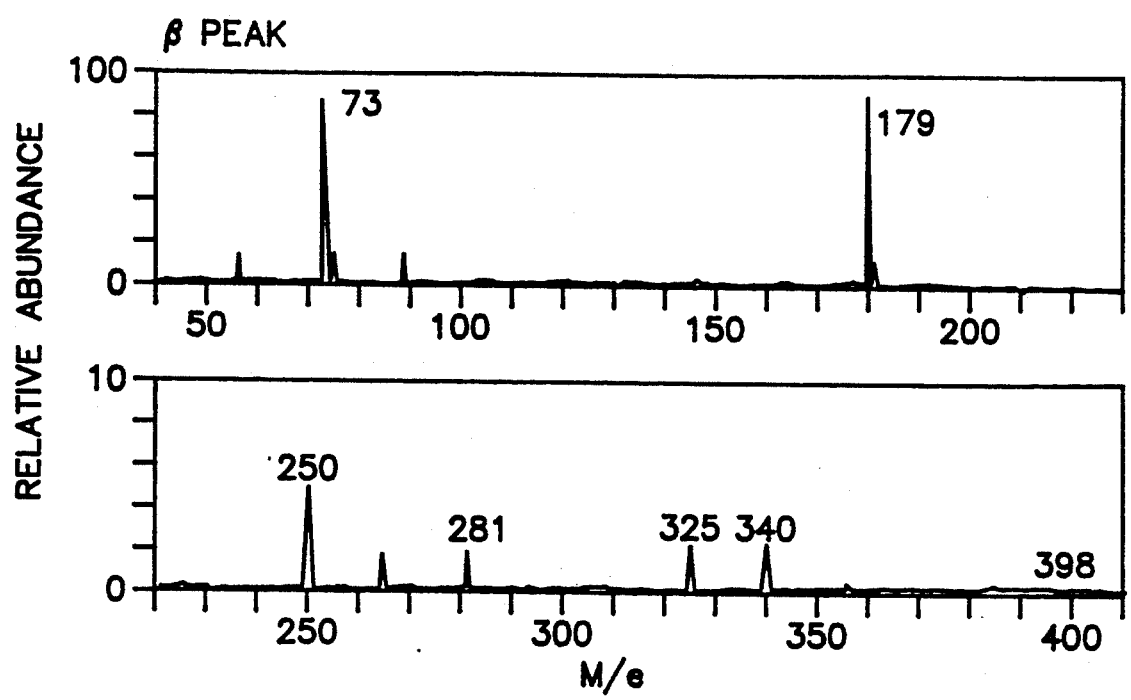
FIG. 7 represents the mass spectra of the trimethylsilyl derivatives of the β peak (A) purified from fetal bovine serum and authentic methyl p-hydroxyphenyllactate (B;MeHPLA).
Figure 7B:
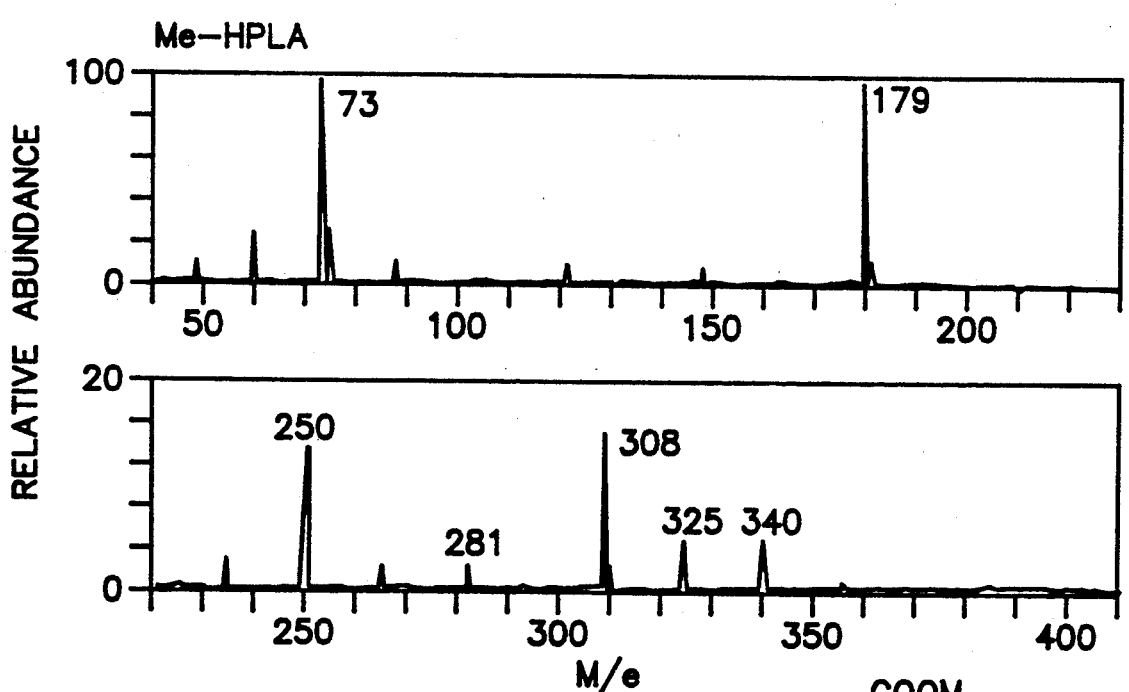
Figure 7B:
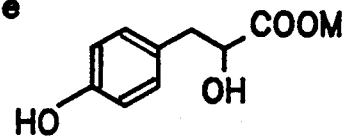

The inhibitor molecules for nuclear Type II sites were isolated from bovine serum. Approximately 500 ml of bovine serum were diluted with an equal volume of HPLC grade water and the pH was adjusted to 1.0 with high purity HCl. The acidified serum was extracted three times with equal volumes of ethyl acetate and the pooled ethyl acetate extracts were dried under vacuum at 60° C. Following evaporation, the extract was redissolved in 100 ml of ethyl acetate and washed with an equal volume of acidified HPLC grade water (pH 1.0). This ethyl acetate fraction was then dried under vacuum, redissolved in the buffer, and chromatographed on a preparative LH-20 column to separate the $\alpha$ and $\beta$ components (FIG. 4). The column fractions were collected and $\alpha$ and $\beta$ peaks were separately pooled, adjusted to pH 1.0, extracted with ethyl acetate, dried, and further purified by HPLC on an Ultrasphere-octyl (C8) reversed phase column (FIG. 5). Structural identification was determined by gas chromatography-mass spectrometry of the trimethylsilyl derivatives of the $\alpha$ and $\beta$ peak components (FIGS. 6 and 7). The $\alpha$ peak component mass spectrum was identical to that of HPLA (FIG. 6). The identity was confirmed with known authentic samples of p-hydroxyphenyllactic acid. The $\beta$ peak component mass spectrum was identified as methyl p-hydroxyphenyllactate (FIG. 7).

Figure 8:
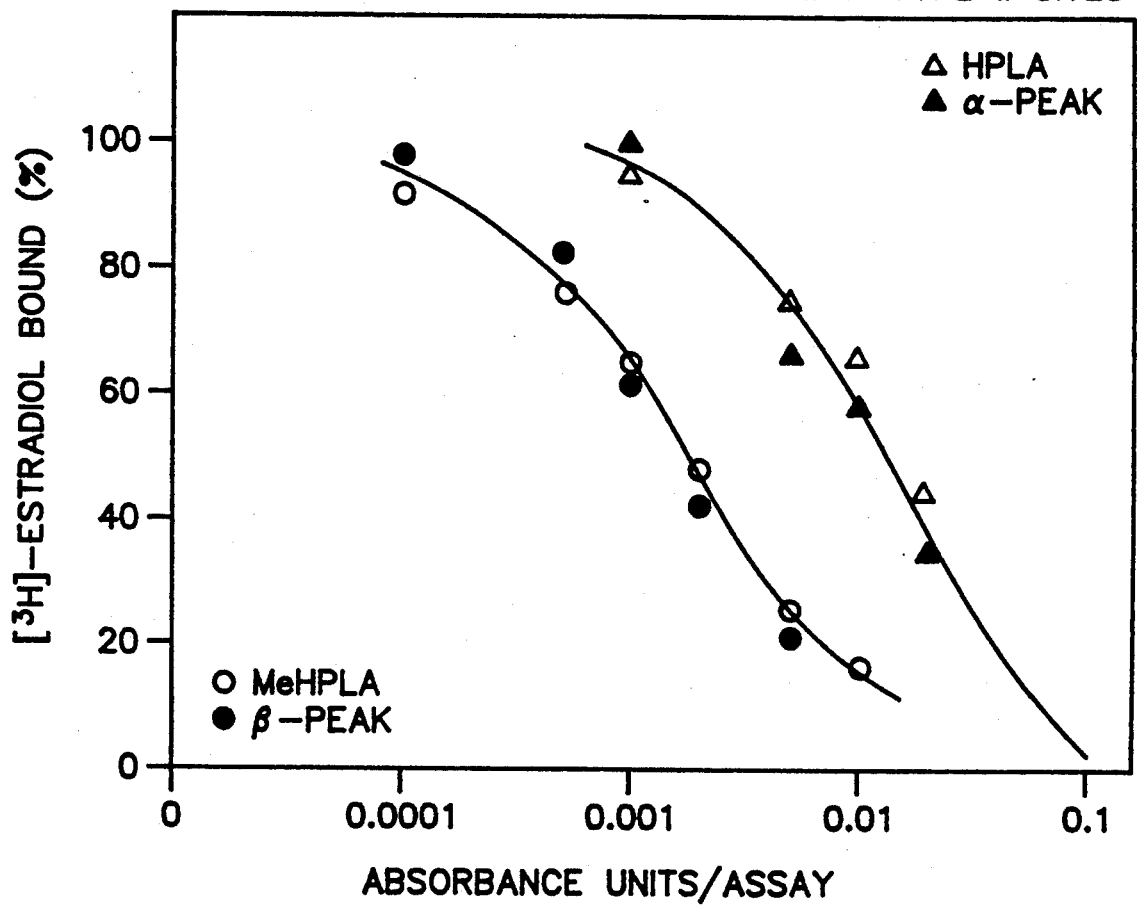
FIG. 8 demonstrates the competition of type II ligand α and β peaks and authentic HPLA and MeHPLA for Type II sites.
Figure 9:
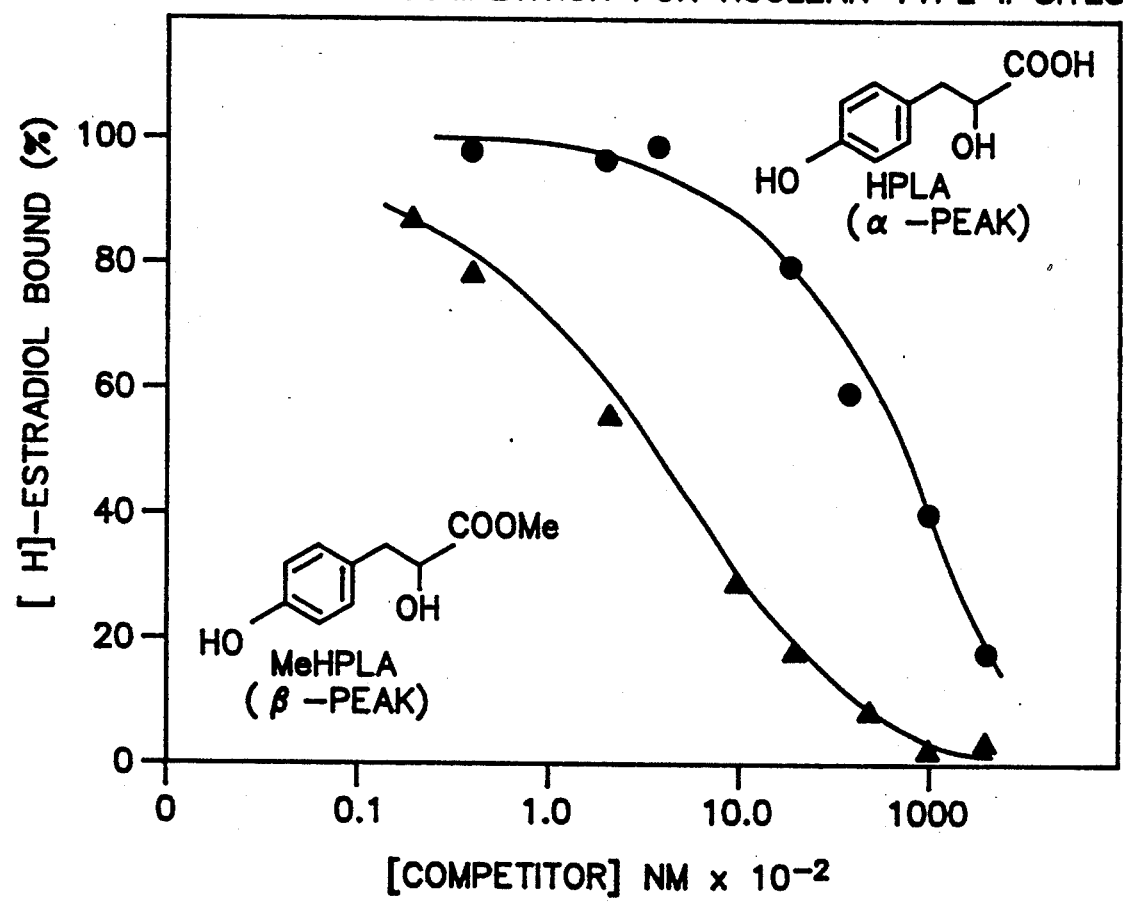
FIG. 9 represents the competition of authentic HPLA and MeHPLA for [$^3$H]estradiol binding to nuclear Type II sites.

Once the peaks were identified, the relative binding with nuclear Type II sites was more precisely determined by competition analysis with known amounts of the two authentic compounds. From FIGS. 8 and 9 it can be seen that MeHPLA is approximately 20-fold more effective in inhibiting [$^3$H]estradiol binding to nuclear Type II sites than the free acid (HPLA).

Figure 10A:
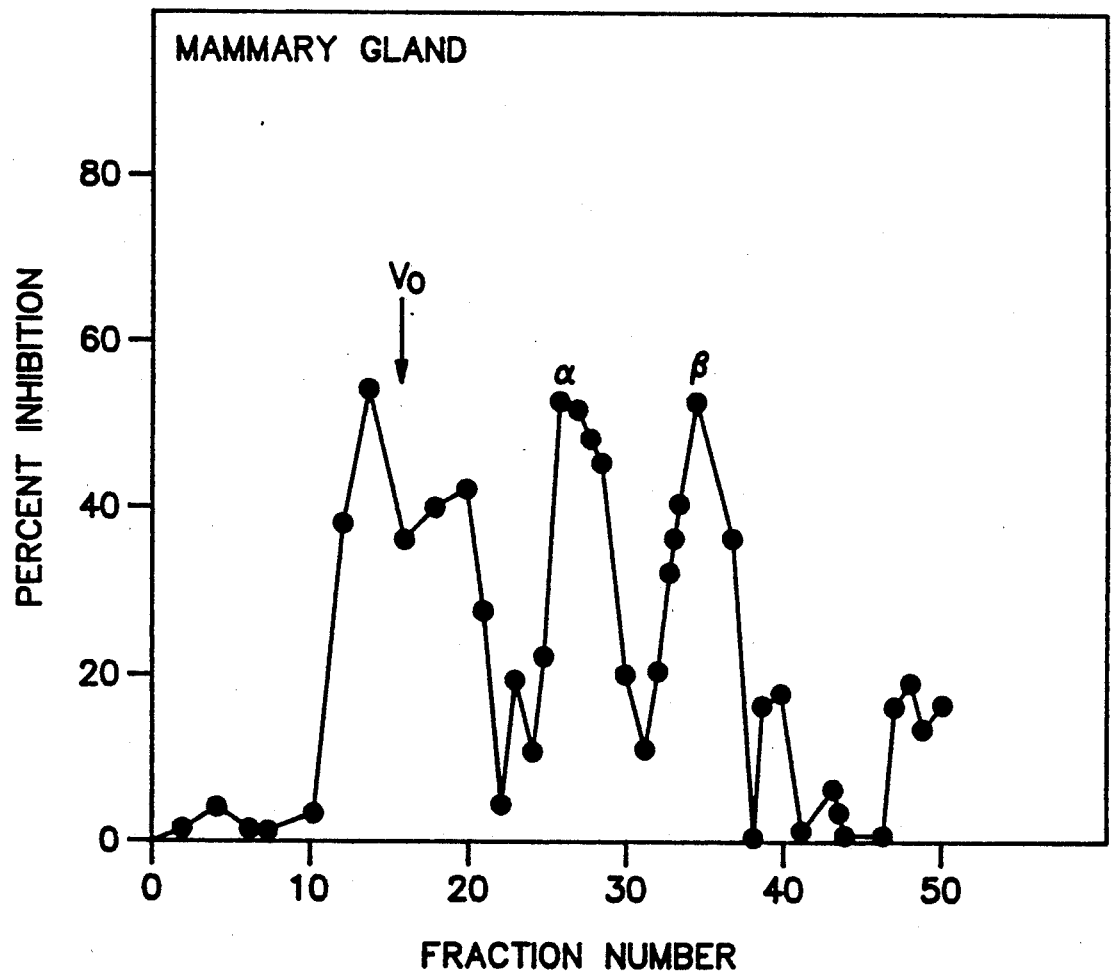
FIG. 10 represents the chromatographic profile of mouse mammary gland (A) and mouse mammary tumor (B) cytosols on LH-20 columns.
Figure 10B:
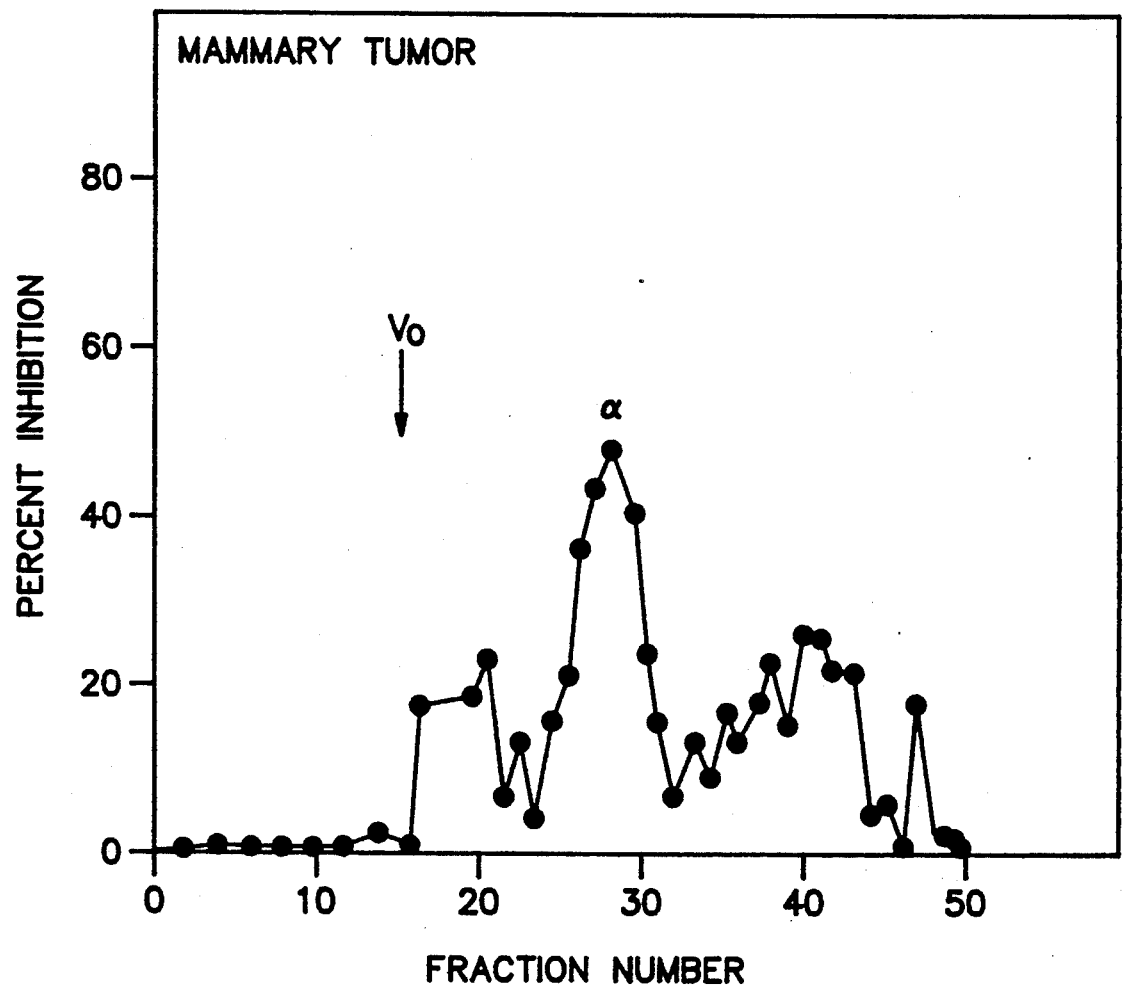
Figure 11:
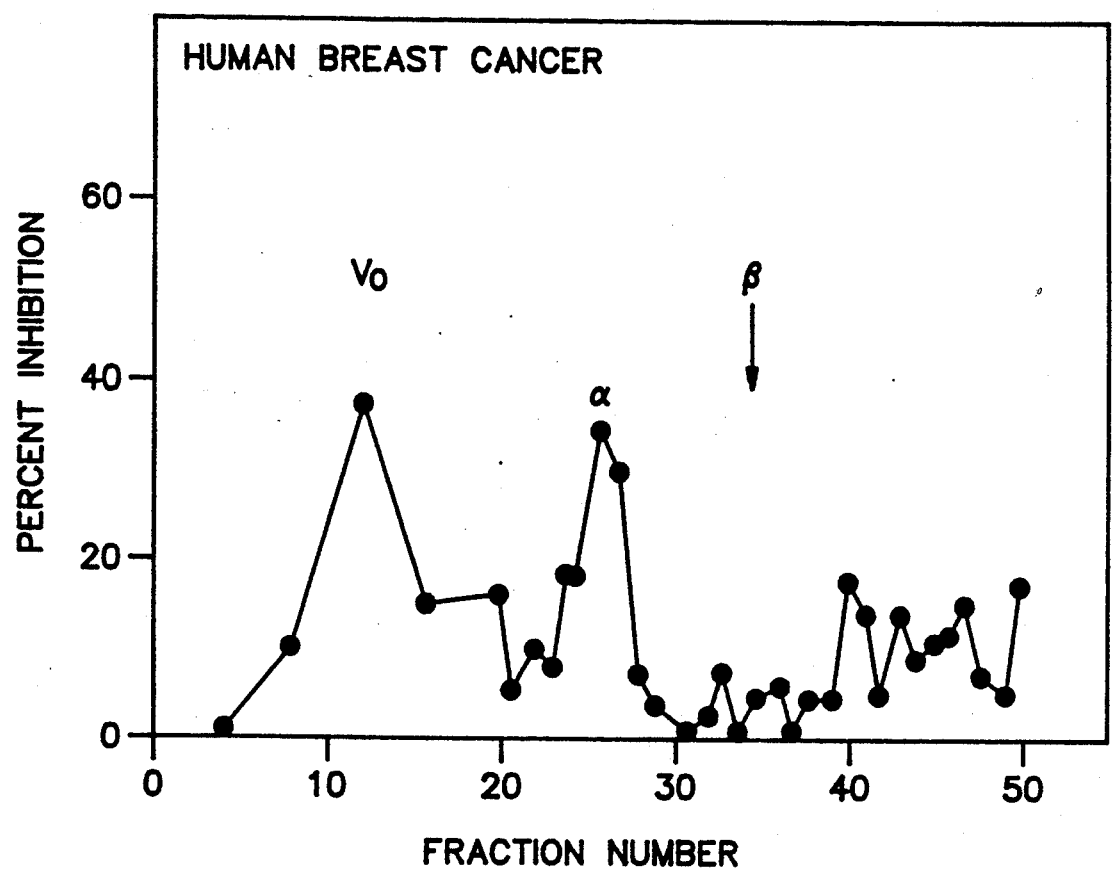
FIG. 11 represents the chromatography of human breast cancer cytosol on an LH-20 column.

Binding assays have shown that the mouse mammary tumor and human breast cancer preparations had high levels of free nuclear Type II sites relative to non-malignant tissues. FIGS. 2 and 10 demonstrate that the normal rat mammary glands contain very high levels of total inhibitor activity relative to mouse mammary tumors. FIG. 11 shows that human breast cancer contains low levels of inhibitor. Thus, the evidence shows that malignant tissues have high levels of free nuclear Type II sites and are deficient in the inhibitor activity. This deficiency in inhibitor activity explains the high levels of free nuclear Type II sites observed in these tumor tissue populations as well as their rapid rate of proliferation, cell growth and DNA synthesis. The high inhibitor activity found in the normal tissues was characterized as previously described on the LH-20 column and revealed that the rat uterus and normal mouse mammary gland contained both $\alpha$ and $\beta$ inhibitor peak components. Comparison of the $\alpha$ and $\beta$ peaks seen in the mouse mammary tumors with those observed in normal tissues showed a high correlation between a deficiency in the $\beta$ peak component and increased unbound nuclear Type II sites in mouse mammary tumor tissue. In the rat and mouse mammary tumor tissues which have been analyzed, the $\beta$ inhibitor component is consistently very low and, in some cases, undetectable. The low to undetectable $\beta$ inhibitor level is also observed in human breast cancer tissue. Examination of a variety of normal tissues, such as rat serum, spleen, diaphragm, liver and uterus, however, shows the presence of both the $\alpha$ and $\beta$ inhibitor peak components. These results demonstrate that the active inhibitor component, with respect to the regulation of cell proliferation, is the $\beta$ inhibitor peak component.

MCF-7 Cancer Cell Assay

Figure 12A:
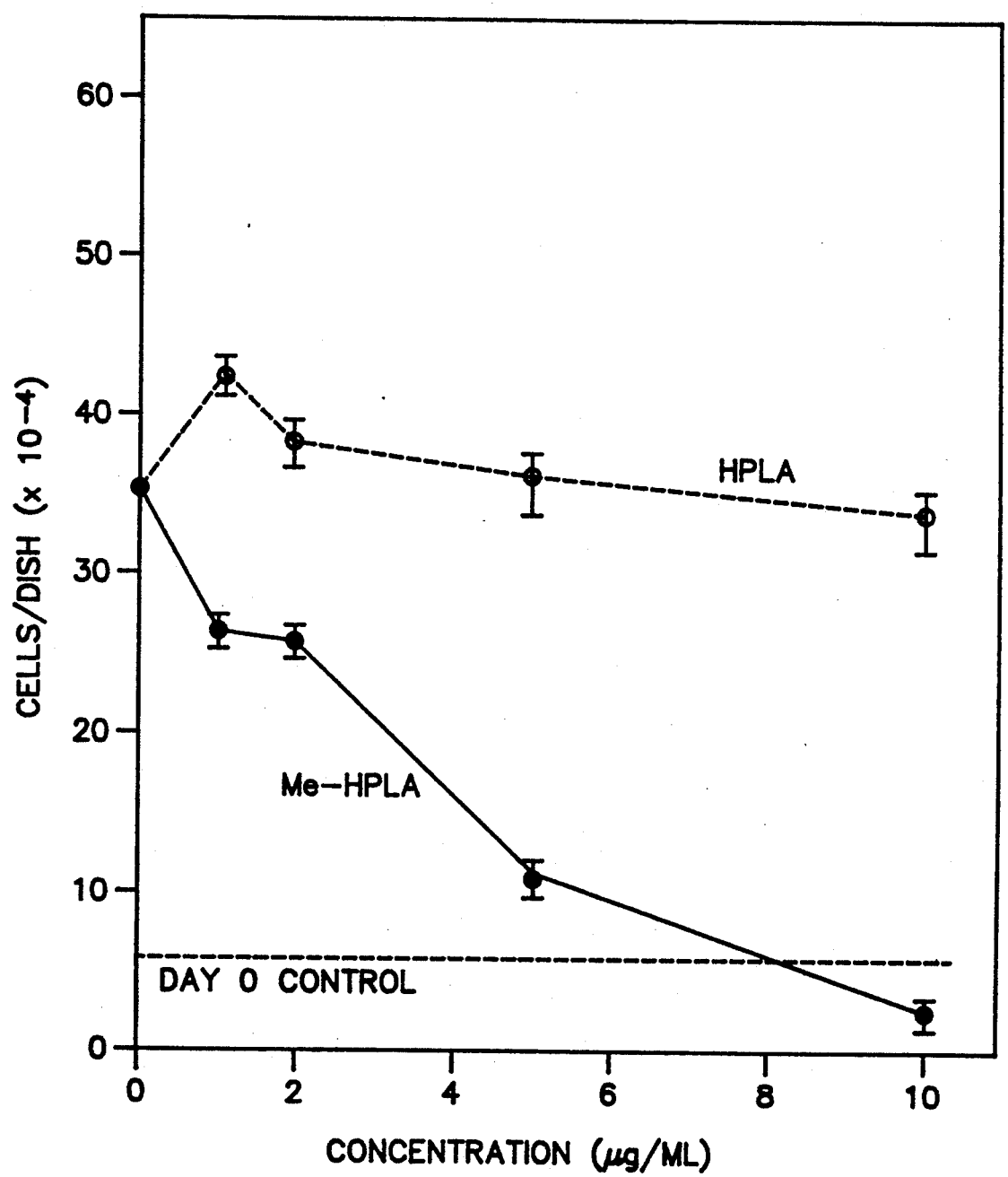
FIG. 12 demonstrates the effects of authentic HPLA and MeHPLA on MCF-7 human breast cancer cell growth.
Figure 12B:
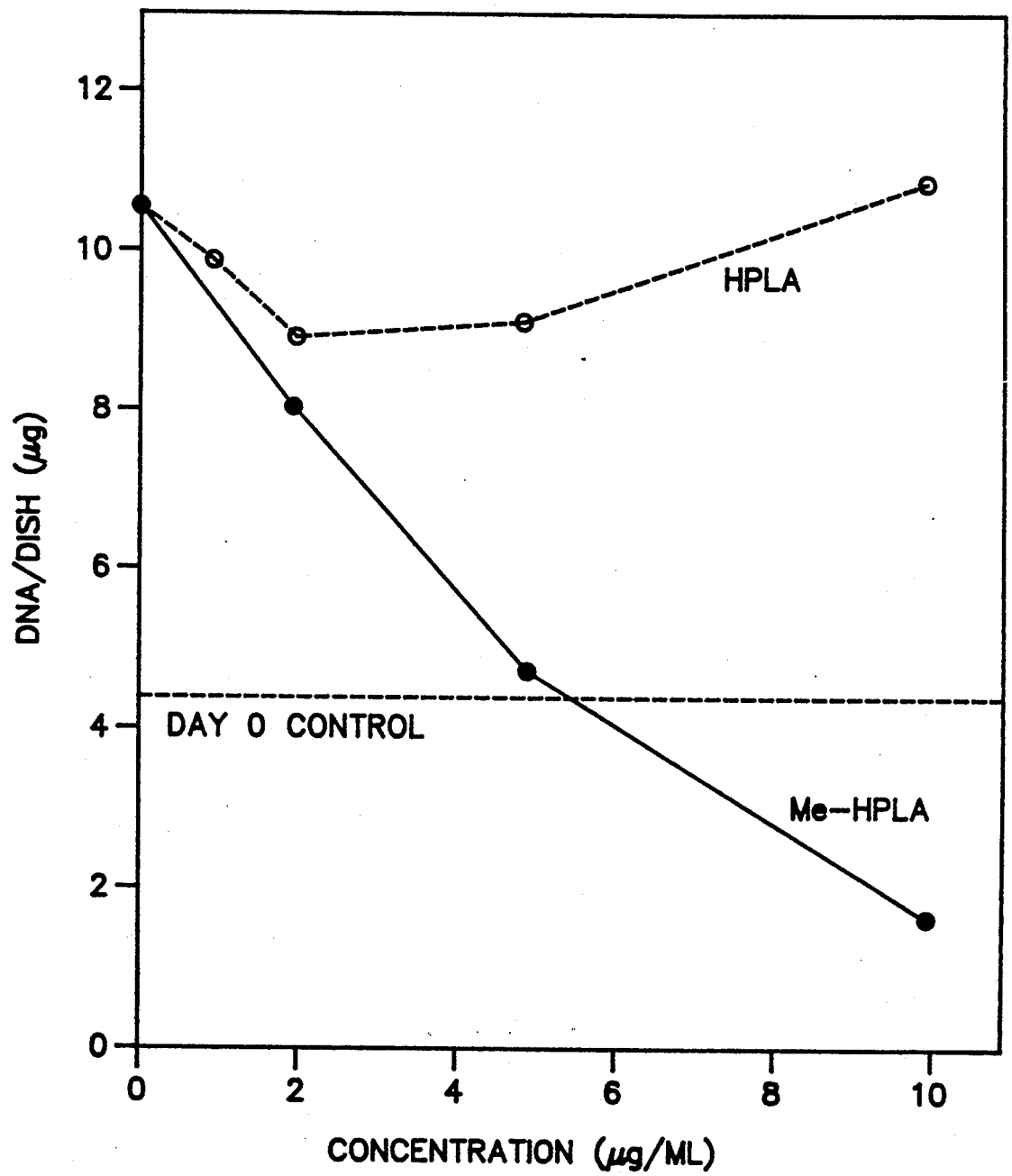

To assay for tumor growth sensitivity the MCF-7 human breast cancer cell line in tissue culture was used. One skilled in the art will recognize that this is an excellent model system to assess the effects of hormones and drugs on human cancer cell growth and proliferation. The MCF-7 cells have both Type I and nuclear Type II estrogen receptor sites and respond in a proliferative fashion to estrogenic hormones. Furthermore, they are inhibited by well-known anti-estrogens such as Tamoxifen. The MCF-7 cells were plated at $5 \times 10^5$ cells/dish in 30 mm petri dishes and grown in Dulbecco's Modified Eagles Medium containing about 10% charcoal stripped fetal bovine serum for approximately 48 hours. During this interval, the cells attached to the plastic dishes and then underwent exponential growth with a cell-doubling time of approximately 24 hours. The plated cells were allowed to attach for approximately 48 hours and the medium was replaced ("day zero"). The cells were allowed to grow exponentially for about 6 days. At day zero the cells were treated with doses ranging from 1–10 µg/ml of the compound of interest, for example, methyl p-hydroxyphenyllactate, in 10 µl of ethanol. The medium was changed at about 2 and 4 days. The control and test solutions were also re-added when the medium was changed. On day 6 the cells were harvested, counted on a hemocytometer and DNA content per dish was determined by the Burton assay (Burton, K., Biochem. J. 62:315–323, 1956). Results are expressed as cells/dish or DNA content (µg/dish) at 6 days following treatment. The results are shown in FIG. 12.

Cultures of rat uterine or mammary tumor cells with cytosol preparations from rat uterus or liver containing $\alpha$ and $\beta$ components showed cell growth inhibition within about 24 hours. Conversely, when the cells were cultured with cytosol preparations from mouse mammary tumors which contained the $\alpha$ but not the $\beta$ component, there was no substantial inhibition of cell growth across the wide range of concentrations tested. These data, consistent with the results of the competition experiments shown on FIGS. 8 and 9, demonstrated that the cytosol preparations from a normal mammary gland contain 15- to 20-fold more total inhibitor activity than those from tumors (FIG. 2). One major difference between cytosol preparations from normal and malignant tissues was that the malignant tissues were deficient in the $\beta$ peak inhibitor component (FIG. 10). Hence, the $\beta$ peak component was the most important compound with respect to potential regulation of cell proliferation. As described in the present invention the $\beta$ peak component was identified as methyl p-hydroxyphenyllactate.

Figure 13A:
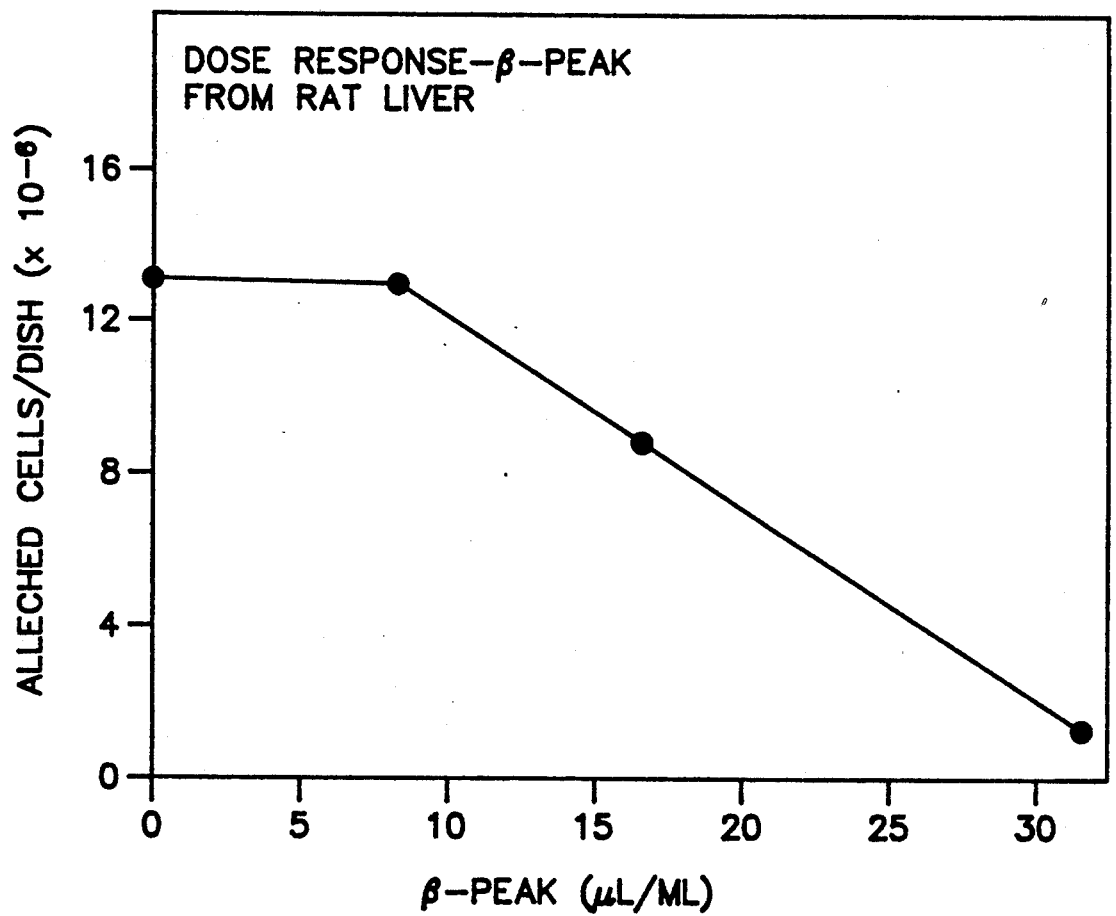
FIG. 13 represents the effects of LH-20 β peak fractions on the growth of MCF-7 human breast cancer cells in culture. Panel A shows the dose response curve for the β peak from rat liver. Panel B shows the time course of inhibition following the addition of 33 μl/ml of the LH-20 β peak fractions.
Figure 13B:
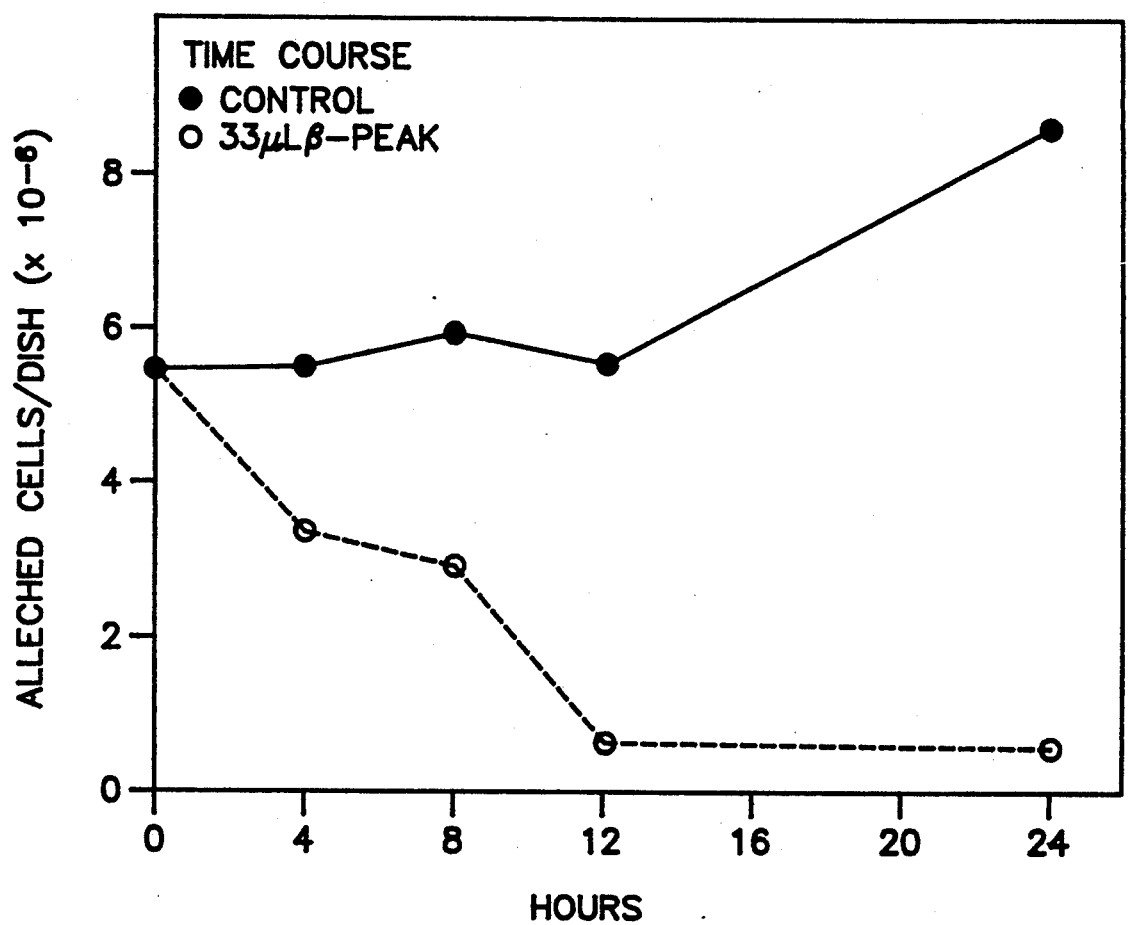

Further, characterization and demonstration of the antitumor activity of the $\beta$ inhibitor component was seen in examples using rat liver isolates. After the isolation, the $\beta$ inhibitor material was suspended in 2 ml of tissue culture medium and added to cultures of MCF-7 human breast cancer cell lines. The MCF-7 cells were plated in 3 ml of DMEM containing 10% charcoal stripped fetal bovine serum and allowed to attach to the surface of petri dishes. Following the establishment of monolayer cultures, approximately 24 to 36 hours, the floating cells were removed by aspiration, and 3 ml of fresh DMEM were added to each culture. At this time various amounts, ranging from 7 to 32 µl/ml, of the pooled $\beta$ peak fractions or control medium were added to the cultures. The cells were cultured for an additional 24 hours. At the end of this culture period, the floating cells were removed by aspiration and the attached cells resuspended in DMEM following mild trypsinization. The cells were then counted on a hemocytometer. With the increasing concentrations of the $\beta$ peak inhibitor material, the cell number was reduced in a dose dependent fashion within about 24 hours (FIG. 13A). The control samples did not exhibit a similar decrease. The time course of the inhibition activity was also examined. Approximately 32 µl of control medium or $\beta$ peak inhibitor material was added to the cells and the floating cells were removed. Within approximately four hours of inhibitor addition, the inhibition of cell growth had begun. Maximum inhibition was observed in approximately 12 hours (FIG. 13B).

The effects of inhibition were reversible. It took approximately 24 hours for the cells to recover and about 7 to 24 days after the removal of the $\beta$ peak inhibitor to regrow to a full monolayer.

It is postulated that tumor cell proliferation is very rapid because the tumor cell metabolizes or inactivates the $\beta$ peak inhibitor. This is supported by the observation that methyl p-hydroxyphenyllactate is found bound to Type II sites in normal tissues but is not found in malignant tissue. Cell proliferation is regulated by ligand binding to nuclear Type II sites. The number of unbound sites determines the rate of proliferation since tumor cells have an increased number of unbound nuclear Type II sites and thus are not inhibited, so tumor cell proliferation is dramatically accelerated. These cells are brought back into regulation and cell proliferation is decreased by administering a therapeutic dose of the inhibitors described in the present invention.

In addition to testing purified biological preparations, the authentic compounds, methyl p-hydroxyphenyllactate and hydroxyphenyllactic acid, were added to cell cultures. As can be seen in FIG. 12, methyl p-hydroxyphenyllactate inhibited MCF-7 human breast cancer cells, but hydroxyphenyllactic acid did not. Furthermore, it can be seen that the methyl p-hydroxyphenyllactate inhibited MCF-7 breast cancer cells in a similar dose-dependent fashion. Results obtained by using the authentic compound were in agreement with the data from biological preparations.

Uterotropic Assay

The rat uterus is exquisitely sensitive to estrogen, and this hormone stimulates uterine cellular hypertrophy, hyperplasia and DNA synthesis within 24 hours following a single injection. Estradiol stimulation of nuclear Type II sites is a prerequisite for these responses. This assay includes injecting immature female rats with saline-ethanol vehicle, estradiol-17$\beta$ and the test compound of interest. Control rats were injected only with saline-ethanol vehicle and estradiol-17$\beta$. The rats were sacrificed 24 hours later and the uterine wet and dry weights were determined. The wet and dry weight measurements are well defined biochemical end points of estrogen action and are a direct index of changes in cell proliferation and DNA synthesis.

The results of these experiments with various compounds are shown in Table I.

Figure 14A:
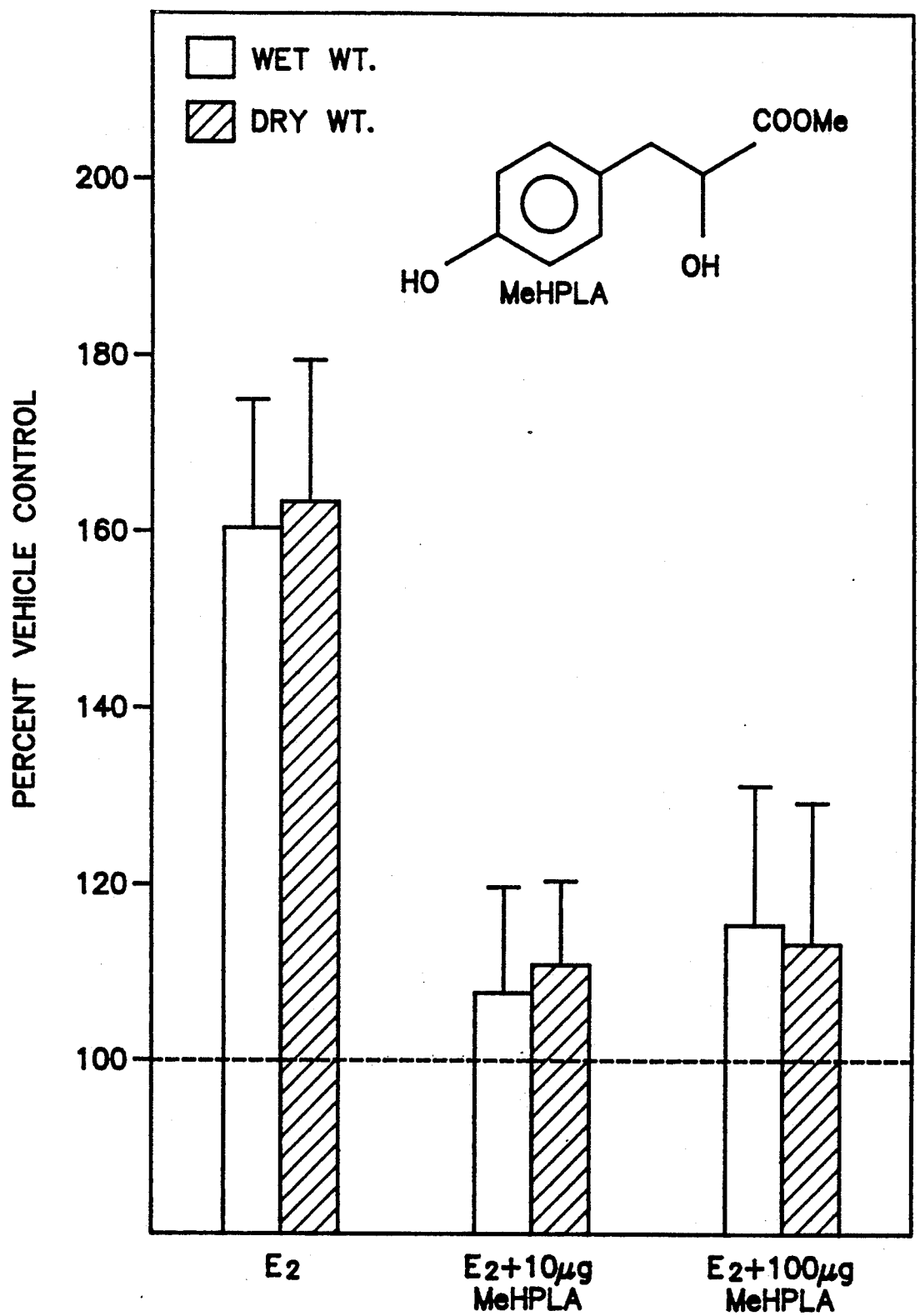
FIG. 14 demonstrates the effects of MeHPLA (A) and HPLA (B) on uterine growth.
Figure 14B:
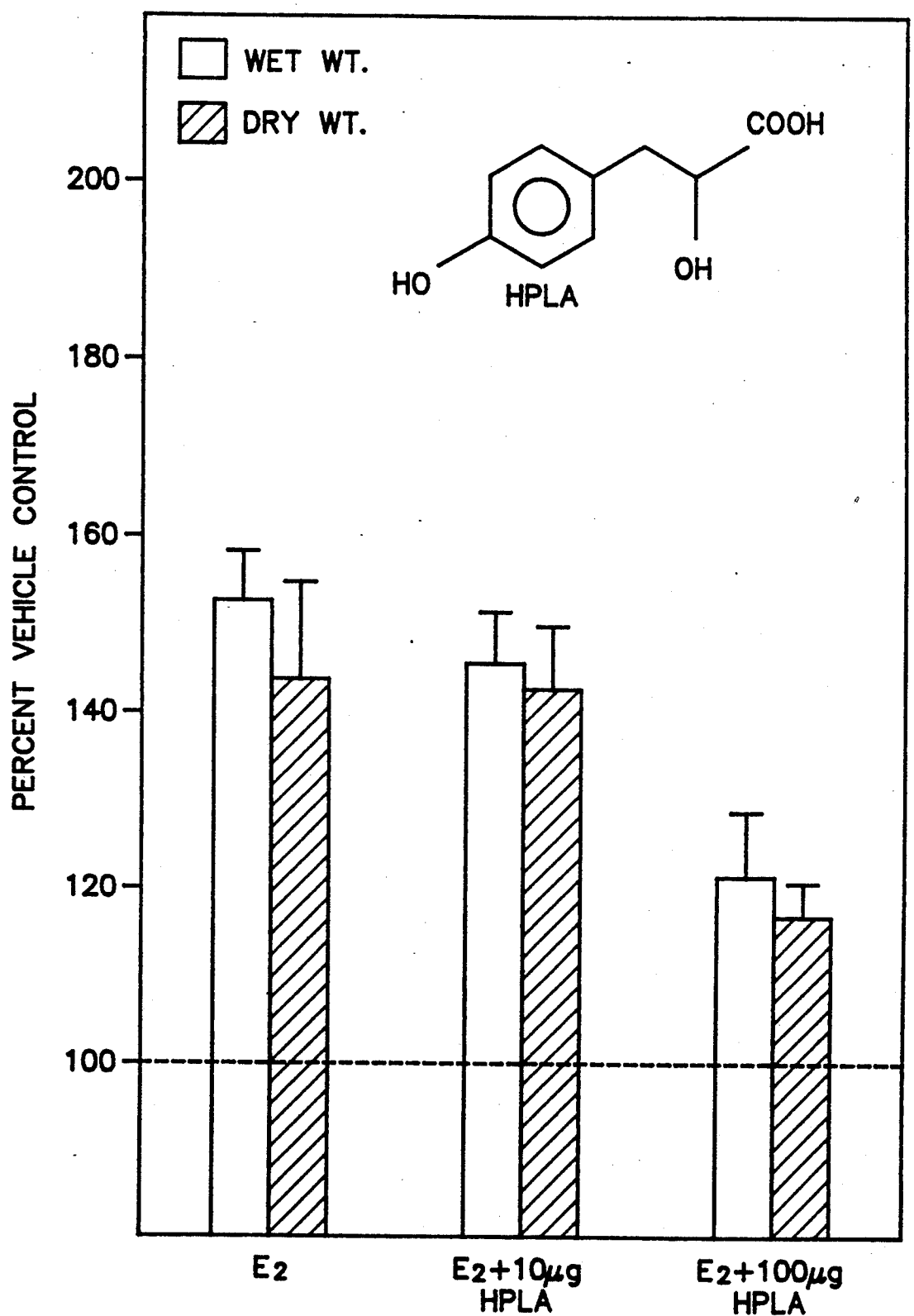

Additional in vivo measurements using the uterotropic assay show the utility of these compounds for inhibiting cell proliferation. Low doses of methyl p-hydroxyphenyllactate, but not hydroxyphenyllactic acid, block estradiol stimulation of uterine growth in the immature rat (FIG. 14 and Table I). However, higher doses of hydroxyphenyllactic acid showed some partial antagonism. This is not surprising since it is known that hydroxyphenyllactic acid binds to nuclear Type II sites with a 20-fold lower affinity than methyl p-hydroxyphenyllactate.

Figure 15:
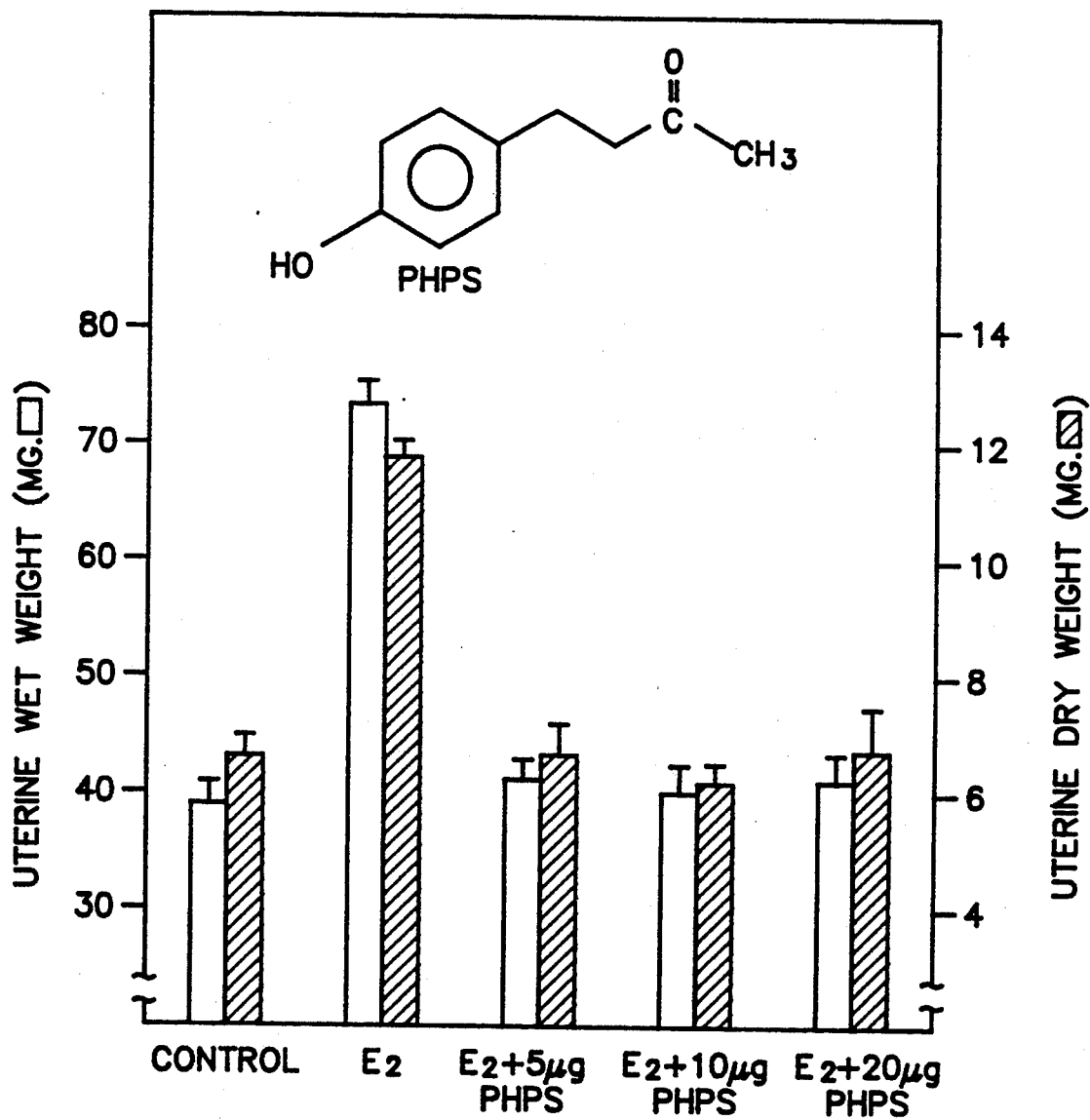
FIG. 15 demonstrates the effects of p-hydroxyphenylbutanone (1(4-hydroxyphenyl)-3-butanone) on uterine growth.

These results demonstrate that the bound/unbound ratio of nuclear Type II sites is important in the regulation of cell growth and that the primary bound inhibitor in normal cells is methyl p-hydroxyphenyllactate. Since the data demonstrated that tumor cells have the ability to inactivate methyl p-hydroxyphenyllactate, the analogues described in this invention were synthesized to avoid this inactivation. Thus, as can be seen in Table I, administration of compounds with various side-chains and various substituents on the aromatic ring resulted in inhibition of uterine growth. One compound 1-(4- hydroxyphenyl)-3-butanone (p-hydroxyphenylbutanone) which includes a C-terminal methyl group is not subject to the esterase cleavage since the methyl group is attached by a C-C bond. This compound is more stable and thus a better inhibitor in culture and in vivo. Furthermore, experiments with 1-(4-hydroxyphenyl)-3-butanone demonstrated that it binds to the nuclear Type II sites with a high affinity and blocks estradiol stimulation of uterine growth when injected into immature rats (FIG. 15). Thus 1-(4-hydroxyphenyl)-3-butanone is an effective inhibitor of tumor growth and regulator of cell proliferation. Table I. MeHPLA Analogue and Related Compound Effects on Uterine Growth and Nuclear Type II Site Binding Inhibition

TABLE I

MeHPLA Analogue and Related Compound Effects on Uterine Growth and Nuclear Type II Site Binding Inhibition

| COMPOUND | GROWTH[a] INHIBITION (%) | TYPE II[b] INHIBITION |
|---|---|---|
| methyl 3-(4-hydroxyphenyl) 2-hydroxypropionate | 90 | 0.8 |
| 3-(4-hydroxyphenyl)-2-hydroxypropionic acid | 0 | 80.0 |
| 1-(4-hydroxyphenyl)-3-butanone | 96 | 2.0 |
| methyl 3-(3,4-dihydroxyphenyl)-2-propenoate | 70 | 1.0 |
| methyl 3-(4-hydroxy-3-methoxyphenyl)-2-propenoate | 56 | 6.0 |
| methyl (4-hydroxyphenoxy) acetate | 70 | 0.8 |

[a] Determined by the ability of the compound (10 μg) to block estradiol stimulation in the rat uterotropic assay.
[b] The concentration (nM) times $10^{-2}$ of the compound to inhibit nuclear Type II binding sites by 50%.

One skilled in the art will readily appreciate that the present invention is well adapted to carry out the objects and obtain the ends and advantages mentioned, as well as those inherent therein. The compounds, methods, procedures and techniques described herein are presently representative of the preferred embodiments, are intended to be exemplary, and are not intended as limitations on the scope of the present invention. Changes therein and other uses will occur to those skilled in the art which are encompassed within the spirit of the invention and are defined by the scope of the appended claims.

What is claimed is:

1. A method of regulating cell growth and proliferation in normal and malignant cells, comprising the step of administering, to an individual in need of said treatment, a therapeutic dose of a compound selected from the group consisting of the formulae:

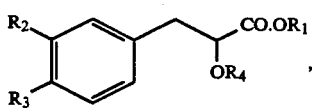

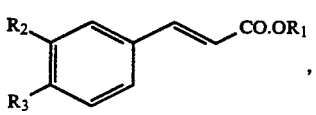

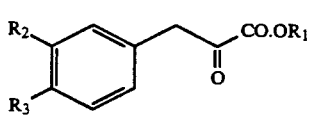

-continued

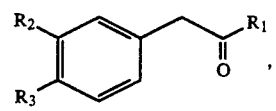

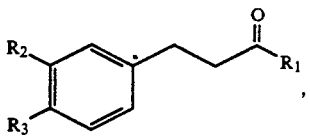

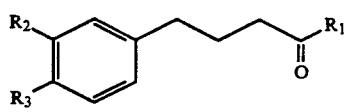

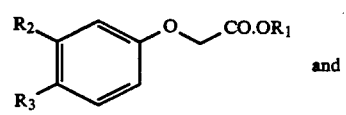

and

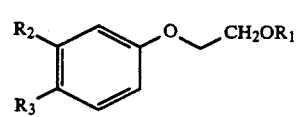

wherein, $R_1$ is selected from the group consisting of H, alkyl groups containing 1 to 6 carbons and aryl groups;

$R_2$ and $R_3$ are not both H and are selected from the group consisting of H, OH and $OCH_3$; and $R_4$ is selected from the group consisting of H and an alkyl group of 1 to 6 carbons.

2. The method of claim 1, wherein said compound is selected from the group consisting of methyl 3-(4-hydroxyphenyl)-2-hydroxypropionate, n-propyl 3-(4-hydroxyphenyl)-2-hydroxypropionate, n-butyl 3-(4-hydroxyphenyl)-2-hydroxypropionate, 3-(4-hydroxyphenyl)-2-propenoic acid, 1-(4-hydroxyphenyl)-3-butanone, 1-(4-hydroxyphenyl)-3-pentanone, methyl-(4-hydroxyphenoxy)acetate, and methyl 3-(3,4-dihydroxyphenyl)-2-propenoate.

3. A method of inhibiting the growth of proliferating cells which include a Type II nuclear estrogen binding site comprising the step of administering, to the proliferating cells, a biologically inhibiting dose of a compound selected from the group consisting of the formulae:

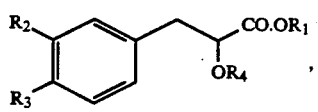

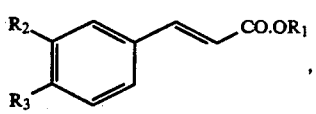

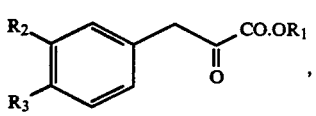

-continued

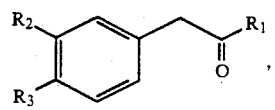

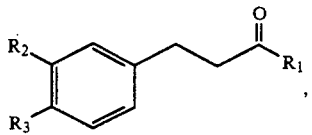

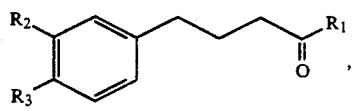

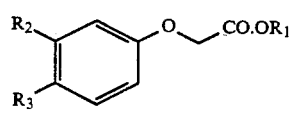 and

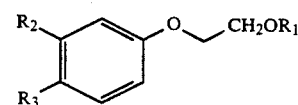
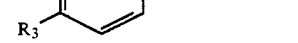

wherein

R$_1$ is selected from the group consisting of H, alkyl group containing 1 to 6 carbons and aryl groups;

R$_2$ and R$_3$ are not both H and are selected from the group consisting of H, OH and OCH$_3$; and R$_4$ is selected from the group consisting of H and an alkyl group of 1 to 6 carbons.

4. The method of claim 3, wherein said compound is selected from the group consisting of methyl 3-(4-hydroxyphenyl)-2-hydroxypropionate, n-propyl 3-(4-hydroxyphenyl)-2-hydroxypropionate, n-butyl 3-(4-hydroxyphenyl)-2-hydroxypropionate, 3-(4-hydroxyphenyl)-2-propenoic acid, 1-(4-hydroxyphenyl)-3-butanone, 1-(4-hydroxyphenyl)-3-pentanone, methyl (4-hydroxyphenoxy)acetate, and methyl 3-(3,4-dihydroxyphenyl)-2-propenoate.

5. The method of claim 3, wherein said proliferating cells are estrogen responsive tissue selected from the group consisting of uterus, mammary gland, uterine tumors and mammary tumors.

6. The method of claim 5, wherein said estrogen responsive tissue is human breast cancer cells.

7. A method for treating benign prostatic hyperplasia, comprising the step of administering a therapeutic dose of a compound selected from the group consisting of the formulae:

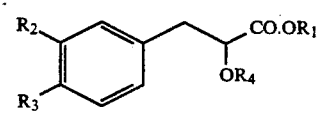

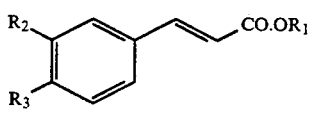

-continued

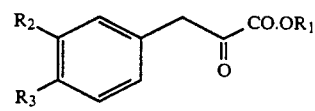

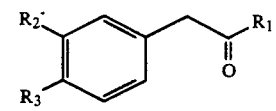

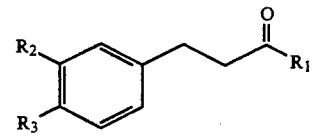

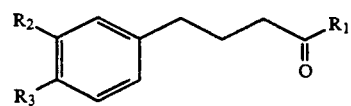

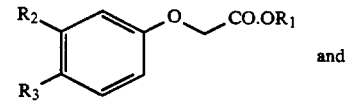 and

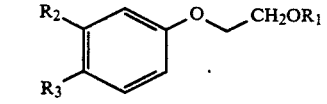

wherein,

R$_1$ is selected from the group consisting of H, alkyl groups containing 1 to 6 carbons and aryl groups;

R$_2$ and R$_3$ are not both H and are selected from the group consisting of H, OH and OCH$_3$; and R$_4$ is selected from the group consisting of H and an alkyl group of 1 to 6 carbons.

8. The method of claim 7, wherein said compound is selected from the group consisting of methyl 3-(4-hydroxyphenyl)-2-hydroxypropionate, n-propyl 3-(4-hydroxyphenyl)-2-hydroxypropionate, n-butyl 3-(4-hydroxyphenyl)-2-hydroxypropionate, 3-(4-hydroxyphenyl)-2-propenoic acid, 1-(4-hydroxyphenyl)-3-butanone, 1-(4-hydroxyphenyl)-3-pentanone, methyl (4-hydroxyphenoxy)acetate, and methyl 3-(3,4-dihydroxyphenyl)-2-propenoate acid.

9. As an agent for regulating cell growth and proliferation in normal and malignant cells, a compound selected from the group consisting of the formulae:

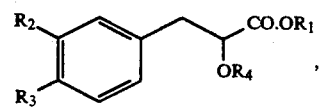

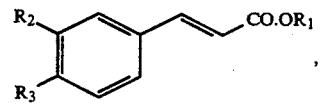

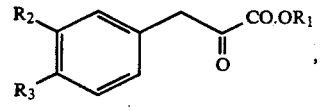

-continued

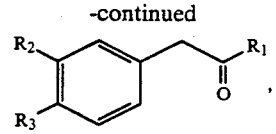

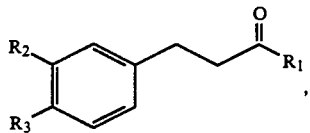

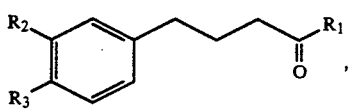

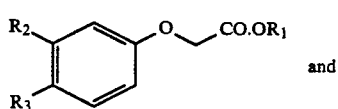

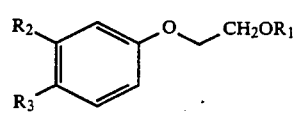

wherein, $R_1$ is selected from the group consisting of H, alkyl groups containing 1 to 6 carbons and aryl groups;

$R_2$ and $R_3$ are not both H and are selected from the group consisting of H, OH and $OCH_3$; and $R_4$ is selected from the group consisting of H and an alkyl group of 1 to 6 carbons.

10. The agent of claim 9, wherein said compound is selected from the group consisting of methyl 3-(4-hydroxyphenyl)-2-hydroxypropionate, n-propyl 3-(4-hydroxyphenyl)-2-hydroxypropionate, n-butyl 3-(4-hydroxyphenyl)-2-hydroxypropionate, 3-(4-hydroxyphenyl)-2-propenoic acid, 1-(4-hydroxyphenyl)-3-butanone, 1-(4-hydroxyphenyl)-3-pentanone, methyl-(4-hydroxyphenoxy)acetate, and methyl 3-(3,4-dihydroxyphenyl)-2-propenoate acid.

11. A method for inhibiting the growth of proliferating cells comprising administration of a biologically inhibiting dose of a compound selected from the group consisting of:

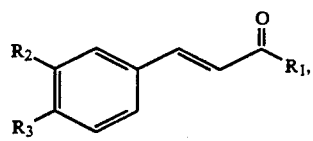

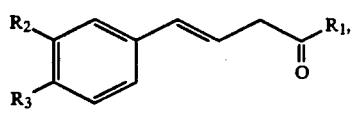

and

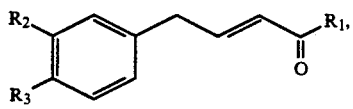

and pharmaceutically acceptable salts thereof, wherein, $R_1$ is selected from the group consisting of H, alkyl groups containing 1 to 6 carbons, and substituted or unsubstituted aryl groups; and $R_2$ and $R_3$ are not both H and are selected from the group consisting of H, OH and $OCH_3$.

12. The method of claim 11 wherein said compound is selected from the group consisting of

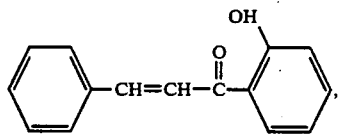

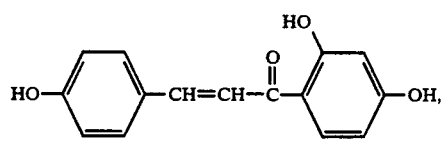

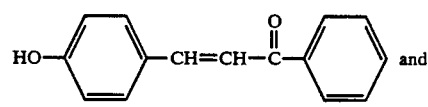

and

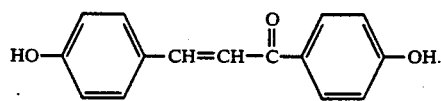

13. The method of claim 11 wherein said compound is selected from the group consisting of 3-(4-Hydroxyphenyl)-1-phenyl-2-propen-1-one and 4-(4-Hydroxyphenyl)-3-buten-2-one, analogs, chemical derivatives and chemically related compounds to the proliferating cells.

14. A method of treating benign prostatic hyperplasia, comprising the administration of a therapeutic dose of a compound selected from the group consisting of:

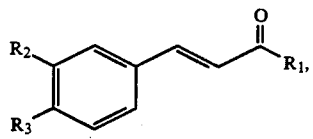

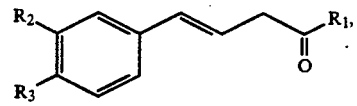

and

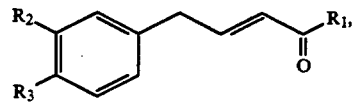

and pharmaceutically acceptable salts thereof, wherein, $R_1$ is selected from the group consisting of H, alkyl groups containing 1 to 6 carbons, and substituted and unsubstituted aryl groups; and $R_2$ and $R_3$ are not both H and are selected from the group consisting of H, OH and $OCH_3$.

15. The method of claim 14, wherein said compound is selected from the group consisting of

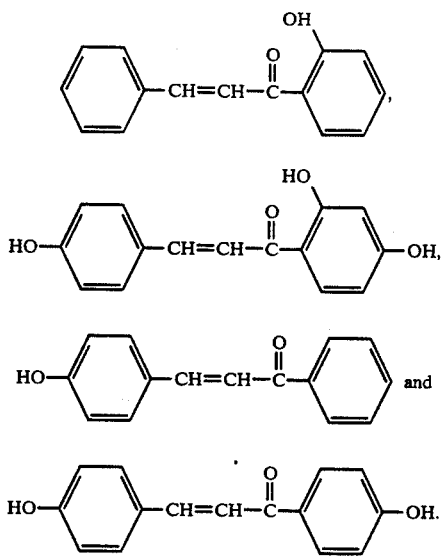

16. The method of claim 14, wherein said compound is selected from the group consisting of 3-(4-Hydroxyphenyl)-1-phenyl-2-propen-1-one and 4-(4-Hydroxyphenyl)-3-buten-2-one, and their analogs, chemical derivatives and chemically related compounds and pharmaceutically related salts thereof.

17. The method of claim 14, wherein said compound is selected from the group consisting of 3-(4-Hydroxyphenyl)-1-phenyl-2-propen-1-one and 4-(4-Hydroxyphenyl)-3-buten-2-one, and pharmaceutically related salts thereof.

18. The method of claim 1, wherein said compound is:

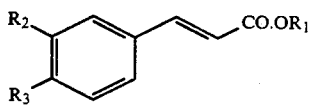

and pharmaceutically acceptable salts thereof, wherein,
$R_1$ is selected from the group consisting of H, alkyl groups containing 1 to 6 carbons and aryl groups; and
$R_2$ and $R_3$ are not both H and are selected from the group consisting of H, OH and $OCH_3$.

19. The method of claim 1, wherein said compound is:

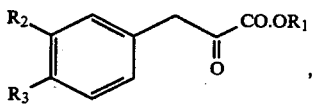

and pharmaceutically acceptable salts thereof, wherein,
$R_1$ is selected from the group consisting of H, alkyl groups containing 1 to 6 carbons and aryl groups; and
$R_2$ and $R_3$ are not both H and are selected from the group consisting of H, OH and $OCH_3$.

20. The method of claim 1, wherein said compound is:

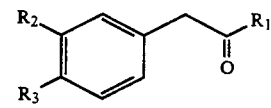

and pharmaceutically acceptable salts thereof, wherein,
$R_1$ is selected from the group consisting of H, alkyl groups containing 1 to 6 carbons and aryl groups; and
$R_2$ and $R_3$ are not both H and are selected from the group consisting of H, OH and $OCH_3$.

21. The method of claim 1, wherein said compound is:

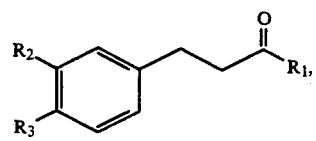

and pharmaceutically acceptable salt thereof, wherein,
$R_1$ is selected from the group consisting of H, alkyl groups containing 1 to 6 carbons and aryl groups; and
$R_2$ and $R_3$ are not both H and are selected from the group consisting of H, OH and $OCH_3$.

22. The method of claim 1, wherein said compound is:

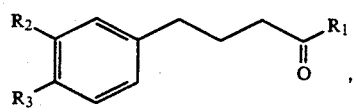

and pharmaceutically acceptable salts thereof, wherein,
$R_1$ is selected from the group consisting of H, alkyl groups containing 1 to 6 carbons and aryl groups; and
$R_2$ and $R_3$ are not both H and are selected from the group consisting of H, OH and $OCH_3$.

23. The method of claim 1, wherein said compound is:

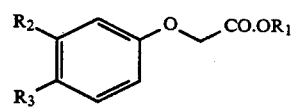

and pharmaceutically acceptable salt thereof, wherein,
$R_1$ is selected from the group consisting of H, alkyl groups containing 1 to 6 carbons and aryl groups; and
$R_2$ and $R_3$ are not both H and are selected from the group consisting of H, OH and $OCH_3$.

24. The method of claim 1, wherein said compound is:

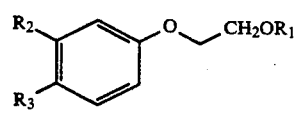

and pharmaceutically acceptable salt thereof, wherein, $R_1$ is selected from the group consisting of H, alkyl groups containing 1 to 6 carbons and aryl groups; and $R_2$ and $R_3$ are not both H and are selected from the group consisting of H, OH and $OCH_3$.

25. The method of claim 3 wherein said compound is:

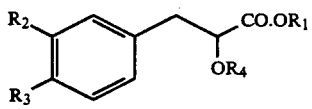

and pharmaceutically acceptable salts thereof, wherein,
$R_1$ is selected from the group consisting of H, alkyl groups containing 1 to 6 carbons and aryl groups;
$R_2$ and $R_3$ are not both H and are selected from the group consisting of H, OH and $OCH_3$; and
$R_4$ selected from the group consisting of H and an alkyl group of 1 to 6 carbons.

26. The method of claim 3 wherein said compound is:

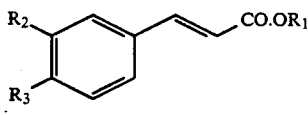

and pharmaceutically acceptable salts thereof, wherein,
$R_1$ is selected from the group consisting of H, alkyl groups containing 1 to 6 carbons and aryl groups; and
$R_2$ and $R_3$ are not both H and are selected from the group consisting of H, OH and $OCH_3$.

27. The method of claim 3 wherein said compound is:

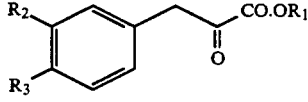

and pharmaceutically acceptable salts thereof, wherein,
$R_1$ is selected from the group consisting of H, alkyl groups containing 1 to 6 carbons and aryl groups; and
$R_2$ and $R_3$ are not both H and are selected from the group consisting of H, OH and $OCH_3$.

28. The method of claim 3 wherein said compound is:

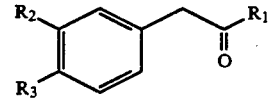

and pharmaceutically acceptable salts thereof, wherein,
$R_1$ is selected from the group consisting of H, alkyl groups containing 1 to 6 carbons and aryl groups; and
$R_2$ and $R_3$ are not both H and are selected from the group consisting of H, OH and $OCH_3$.

29. The method of claim 3 wherein said compound is:

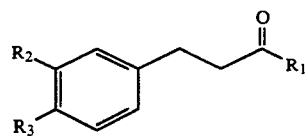

and pharmaceutically acceptable salts thereof, wherein,
$R_1$ is selected from the group consisting of H, alkyl groups containing 1 to 6 carbons and aryl groups; and
$R_2$ and $R_3$ are not both H and are selected from the group consisting of H, OH and $OCH_3$.

30. The method of claim 3 wherein said compound is:

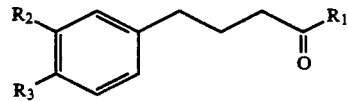

and pharmaceutically accetable salts thereof, wherein,
$R_1$ is selected from the group consisting of H, alkyl groups containing 1 to 6 carbons and aryl groups; and
$R_2$ and $R_3$ are not both H and are selected from the group consisting of H, OH and $OCH_3$.

31. The method of claim 3 wherein said compound is:

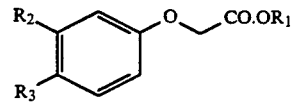

and pharmaceutically acceptable salts thereof, wherein,
$R_1$ is selected from the group consisting of H, alkyl groups containing 1 to 6 carbons and aryl groups; and
$R_2$ and $R_3$ are not both H and are selected from the group consisting of H, OH and $OCH_3$.

32. The method of claim 3 wherein said compound is:

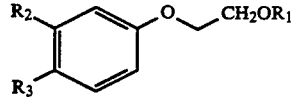

and pharmaceutically acceptable salts thereof wherein,
$R_1$ is selected from the group consisting of H, alkyl groups containing 1 to 6 carbons and aryl groups; and
$R_2$ and $R_3$ are not both H and are selected from the group consisting of H, OH and $OCH_3$.

33. The method of claim 2, wherein said compound is methyl 3-(4-hydroxyphenyl)-2-hydroxypropionate.

34. The method of claim 2, wherein said compound is n-propyl 3-(4-hydroxyphenyl)-2-hydroxypropionate.

35. The method of claim 2, wherein said compound is n-butyl 3-(4-hydroxyphenyl)-2-hydroxypropionate.

36. The method of claim 2, wherein said compound is 3-(4-hydroxyphenyl)-2-propenoic acid.

37. The method of claim 2, wherein said compound is 1-(4-hydroxyphenyl)-3-butanone.

38. The method of claim 2, wherein said compound is 1-(4-hydroxyphenyl)-3-pentanone.

39. The method of claim 2, wherein said compound is methyl-(4-hydroxyphenoxy)acetate.

40. The method of claim 2, wherein said compound is methyl 3-(3,4-dihydroxyphenyl)-2-propenoate.

41. The method of claim 4, wherein said compound is methyl 3-(4-hydroxyphenyl)-2-hydroxypropionate.

42. The method of claim 4, wherein said compound is n-propyl 3-(4-hydroxyphenyl)-2-hydroxypropionate.

43. The method of claim 4, wherein said compound is n-butyl 3-(4-hydroxyphenyl)-2-hydroxypropionate.

44. The method of claim 4, wherein said compound is 3-(4-hydroxyphenyl)-2-propenoic acid.

45. The method of claim 4, wherein said compound is 1-(4-hydroxyphenyl)-3-butanone.

46. The method of claim 4, wherein said compound is 1-(4-hydroxyphenyl)-3-pentanone.

47. The method of claim 4, wherein said compound is methyl-(4-hydroxyphenoxy)acetate.

48. The method of claim 4, wherein said compound is methyl 3-(3,4-dihydroxyphenyl)-2-propenoate.

49. The method of claim 7 wherein said compound is:

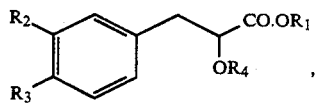

and pharmaceutically acceptable salts thereof, wherein,
$R_1$ is selected from the group consisting of H, alkyl groups containing 1 to 6 carbons and aryl groups;
$R_2$ and $R_3$ are not both H and are selected from the group consisting of H, OH and $OCH_3$; and
$R_4$ selected from the group consisting of H and an alkyl group of 1 to 6 carbons.

50. The method of claim 7 wherein said compound is:

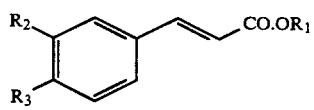

and pharmaceutically acceptable salts thereof wherein,
$R_1$ is selected from the group consisting of H, alkyl groups containing 1 to 6 carbons and aryl groups; and
$R_2$ and $R_3$ are not both H and are selected from the group consisting of H, OH and $OCH_3$.

51. The method of claim 7 wherein said compound is:

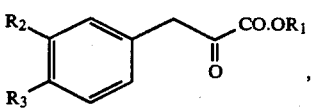

and pharmaceutically acceptable salts thereof, wherein,
$R_1$ is selected from the group consisting of H, alkyl groups containing 1 to 6 carbons and aryl groups; and
$R_2$ and $R_3$ are not both H and are selected from the group consisting of H, OH and $OCH_3$.

52. The method of claim 7 wherein said compound is:

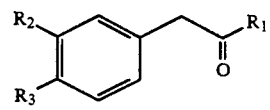

and pharmaceutically acceptable salts thereof, wherein,
$R_1$ is selected from the group consisting of H, alkyl groups containing 1 to 6 carbons and aryl groups; and
$R_2$ and $R_3$ are not both H and are selected from the group consisting of H, OH and $OCH_3$.

53. The method of claim 7 wherein said compound is:

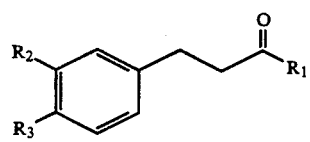

and pharmaceutically acceptable salts thereof, wherein,
$R_1$ is selected from the group consisting of H, alkyl groups containing 1 to 6 carbons and aryl groups; and
$R_2$ and $R_3$ are not both H and are selected from the group consisting of H, OH and $OCH_3$.

54. The method of claim 7 wherein said compound is:

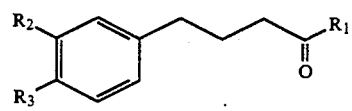

and pharmaceutically acceptable salts thereof, wherein,
$R_1$ is selected from the group consisting of H, alkyl groups containing 1 to 6 carbons and aryl groups; and
$R_2$ and $R_3$ are not both H and are selected from the group. consisting of H, OH and $OCH_3$.

55. The method of claim 7 wherein said compound is:

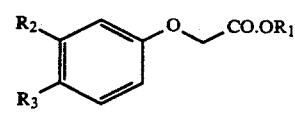

and pharmaceutically acceptable salts thereof, wherein,
$R_1$ is selected from the group consisting of H, alkyl groups containing 1 to 6 carbons and aryl groups; and
$R_2$ and $R_3$ are not both H and are selected from the group consisting of H, OH and $OCH_3$.

56. The method of claim 7 wherein said compound is:

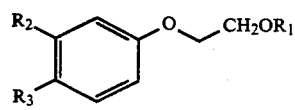

and pharmaceutically acceptable salts thereof, wherein,
$R_1$ is selected from the group consisting of H, alkyl groups containing 1 to 6 carbons and aryl groups; and
$R_2$ and $R_3$ are not both H and are selected from the group consisting of H, OH and $OCH_3$.

57. The method of claim 7, wherein said compound is methyl 3-(4-hydroxyphenyl)-2-hydroxypropionate.

58. The method of claim 7, wherein said compound is n-propyl 3-(4-hydroxyphenyl)-2-hydroxypropionate.

59. The method of claim 7, wherein said compound is n-butyl 3-(4-hydroxyphenyl)-2-hydroxypropionate.

60. The method of claim 7, wherein said compound is 3-(4-hydroxyphenyl)-2-propenoic acid.

61. The method of claim 7, wherein said compound is 1-(4-hydroxyphenyl)-3-butanone.

62. The method of claim 7, wherein said compound is 1-(4-hydroxyphenyl)-3-pentanone.

63. The method of claim 7, wherein said compound is methyl-(4-hydroxyphenoxy)acetate.

64. The method of claim 7, wherein said compound is methyl 3-(3,4-dihydroxyphenyl)-2-propenoate.

65. The method of claim 11 wherein said compound is:

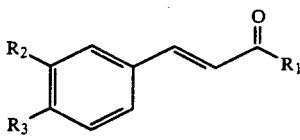

and pharmaceutically acceptable salts thereof wherein,
$R_1$ is selected from the group consisting of H, alkyl groups containing 1 to 6 carbons and substituted or unsubstituted aryl groups;
$R_2$ and $R_3$ are not both H and are selected from the group consisting of H, OH and $OCH_3$.

66. The method of claim 11 wherein said compound is:

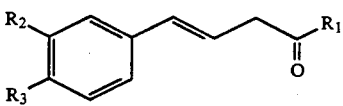

and pharmaceutically acceptable salts thereof wherein,
$R_1$ is selected from the group consisting of H, alkyl groups containing 1 to 6 carbons and substituted or unsubstituted aryl groups;
$R_2$ and $R_3$ are not both H and are selected from the group consisting of H, OH and $OCH_3$.

67. The method of claim 11 wherein said compound is:

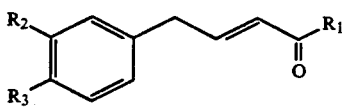

and pharmaceutically acceptable salts thereof wherein,
$R_1$ is selected from the group consisting of H, alkyl groups containing 1 to 6 carbons and substituted or unsubstituted aryl groups;
$R_2$ and $R_3$ are not both H and are selected from the group consisting of H, OH and $OCH_3$.

68. The method of claim 11 wherein said compound is:

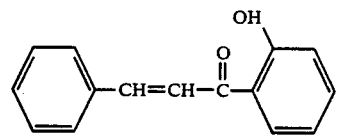

and pharmaceutically acceptable salts thereof.

69. The method of claim 11 wherein said compound is:

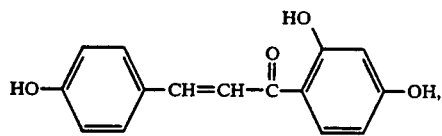

and pharmaceutically acceptable salts thereof.

70. The method of claim 11 wherein said compound is:

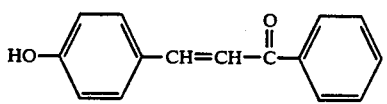

and pharmaceutically acceptable salts thereof.

71. The method of claim 11 wherein said compound is:

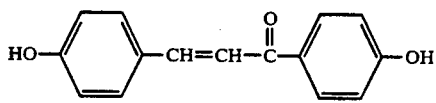

and pharmaceutically acceptable salts thereof.

72. The method of claim 14 wherein said compound is:

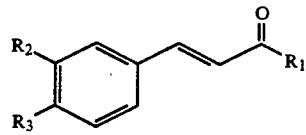

and pharmaceutically acceptable salts thereof wherein,
$R_1$ is selected from the group consisting of H, alkyl groups containing 1 to 6 carbons and substituted or unsubstituted aryl groups; and
$R_2$ and $R_3$ are not both H and are selected from the group consisting of H, OH and $OCH_3$.

73. The method of claim 14 wherein said compound is:

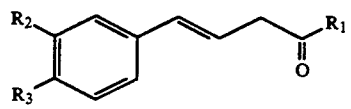

and pharmaceutically acceptable salts thereof wherein,
$R_1$ is selected from the group consisting of H, alkyl groups containing 1 to 6 carbons and substituted or unsubstituted aryl groups; and $R_2$ and $R_3$ are not both H and are selected from the group consisting of H, OH and OCH$_3$.

74. The method of claim 14 wherein said compound is:

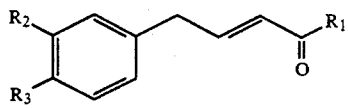

and pharmaceutically acceptable salts thereof wherein, $R_1$ is selected from the group consisting of H, alkyl groups containing 1 to 6 carbons and substituted or unsubstituted aryl groups; and $R_2$ and $R_3$ are not both H and are selected from the group consisting of H, OH and OCH$_3$.

75. The method of claim 14 wherein said compound is:

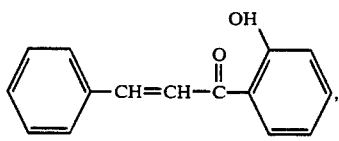

and pharmaceutically acceptable salts thereof.

76. The method of claim 14 wherein said compound is:

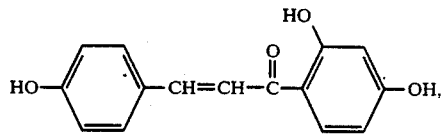

and pharmaceutically acceptable salts thereof.

77. The method of claim 14 wherein said compound is:

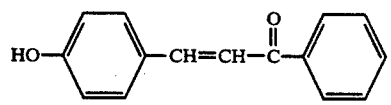

and pharmaceutically acceptable salts thereof.

78. The method of claim 14 wherein said compound is:

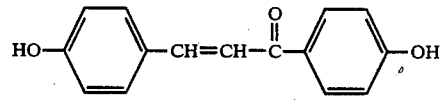

and pharmaceutically acceptable salts thereof.

* * * * *